(12) United States Patent
Ignon et al.

(10) Patent No.: US 10,357,641 B2
(45) Date of Patent: *Jul. 23, 2019

(54) TIPS FOR SKIN TREATMENT DEVICE

(71) Applicant: EDGE SYSTEMS LLC, Signal Hill, CA (US)

(72) Inventors: Roger Ignon, Redondo Beach, CA (US); Scott Mallett, Coto De Caza, CA (US); Abraham Solano, Corona, CA (US); William Cohen, Los Alamitos, CA (US)

(73) Assignee: Edge Systems LLC, Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/660,750

(22) Filed: Jul. 26, 2017

(65) Prior Publication Data
US 2017/0319835 A1 Nov. 9, 2017

Related U.S. Application Data

(63) Continuation of application No. 14/700,789, filed on Apr. 30, 2015, now Pat. No. 9,814,868, which is a
(Continued)

(51) Int. Cl.
*A61B 17/54* (2006.01)
*A61M 35/00* (2006.01)
(Continued)

(52) U.S. Cl.
CPC ....... *A61M 35/003* (2013.01); *A61B 17/3205* (2013.01); *A61B 17/50* (2013.01);
(Continued)

(58) Field of Classification Search
CPC ........ A61M 35/003; A61M 2037/0007; A61N 5/0616; A61B 17/54; A61B 17/545;
(Continued)

(56) References Cited

U.S. PATENT DOCUMENTS 1,651,585 A 12/1927 Clair
2,608,032 A 8/1952 Garver
(Continued)

FOREIGN PATENT DOCUMENTS

AT 400 305 12/1995
AU 1 014 299 5/1999
(Continued)

OTHER PUBLICATIONS (English abstract of WO 2004/037098), Feb. 2, 2006, Bionoface.
(Continued)

*Primary Examiner* — Ryan J. Severson
*Assistant Examiner* — Christian D Knauss
(74) *Attorney, Agent, or Firm* — Knobbe, Martens, Olson & Bear, LLP

(57) ABSTRACT

An apparatus for treating skin has a console with a user input device and a handpiece assembly. The handpiece assembly is configured to treat skin. A fluid line provides fluid communication between the console and the handpiece assembly. A manifold system is coupled to the console and controlled by the user input device. The manifold system is configured to hold releasably a plurality of fluid sources and deliver fluid from at least one of the plurality of fluid sources to the handpiece assembly.

18 Claims, 25 Drawing Sheets

Related U.S. Application Data continuation of application No. 13/267,554, filed on Oct. 6, 2011, now Pat. No. 9,474,886, which is a continuation of application No. 11/392,348, filed on Mar. 29, 2006, now Pat. No. 8,048,089.

(60) Provisional application No. 60/755,310, filed on Dec. 30, 2005, provisional application No. 60/764,668, filed on Feb. 2, 2006.

(51) Int. Cl.

| | | |
|---|---|---|
| *A61M 1/00* | (2006.01) | |
| *A61B 17/3205* | (2006.01) | |
| *A61B 17/50* | (2006.01) | |
| *A61B 50/10* | (2016.01) | |
| *A61B 50/13* | (2016.01) | |
| *A61M 37/00* | (2006.01) | |
| *A61B 17/00* | (2006.01) | |
| *A61N 5/06* | (2006.01) | |
| *A61B 17/32* | (2006.01) | |

(52) U.S. Cl.
CPC .......... *A61B 17/54* (2013.01); *A61B 17/545* (2013.01); *A61B 50/10* (2016.02); *A61B 50/13* (2016.02); *A61M 1/009* (2014.02); *A61M 37/00* (2013.01); *A61B 2017/00199* (2013.01); *A61B 2017/00761* (2013.01); *A61B 2017/320004* (2013.01); *A61B 2217/005* (2013.01); *A61M 2037/0007* (2013.01); *A61N 5/0616* (2013.01)

(58) Field of Classification Search
CPC .......... A61B 2017/00535; A61B 2017/00561; A61B 2017/00761; A61B 2017/320004; A61B 2017/320008; A61B 2017/320012; A61B 2217/005

See application file for complete search history.

(56) References Cited

U.S. PATENT DOCUMENTS

| | | |
|---|---|---|
| 2,631,583 A | 3/1953 | Lavergne |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,037,509 A | 6/1962 | Schutz |
| 3,085,573 A | 4/1963 | Meyer et al. |
| 3,214,869 A | 11/1965 | Stryker |
| 3,468,079 A | 9/1969 | Kaufman |
| 3,476,112 A | 11/1969 | Elstein |
| 3,481,677 A | 12/1969 | Abrahamson |
| 3,505,993 A | 4/1970 | Lewes et al. |
| 3,574,239 A | 4/1971 | Sollerud |
| 3,715,838 A | 2/1973 | Young et al. |
| 3,865,352 A | 2/1975 | Nelson et al. |
| 3,866,264 A | 2/1975 | Engquist |
| 3,948,265 A | 4/1976 | Al Ani |
| 3,964,212 A | 6/1976 | Karden |
| 3,968,789 A | 7/1976 | Simoncini |
| 3,977,084 A | 8/1976 | Sloan |
| 4,121,388 A | 10/1978 | Wilson |
| 4,155,721 A | 5/1979 | Fletcher |
| 4,170,821 A | 10/1979 | Booth |
| 4,182,329 A | 1/1980 | Smit et al. |
| 4,203,431 A | 5/1980 | Abura et al. |
| 4,216,233 A | 8/1980 | Stein |
| 4,225,254 A | 9/1980 | Holberg et al. |
| 4,289,158 A | 9/1981 | Nehring |
| 4,299,219 A | 11/1981 | Norris, Jr. |
| 4,378,804 A | 4/1983 | Cortese |
| 4,560,373 A | 12/1985 | Sugino et al. |
| 4,646,480 A | 3/1987 | Williams |
| 4,646,482 A | 3/1987 | Chitjian |
| 4,655,743 A | 4/1987 | Hyde |
| 4,676,749 A | 6/1987 | Mabille |
| 4,706,676 A | 11/1987 | Peck |
| 4,718,467 A | 1/1988 | Di Gianfilippo et al. |
| 4,754,756 A | 7/1988 | Shelanski |
| 4,757,814 A | 7/1988 | Wang et al. |
| 4,764,362 A | 8/1988 | Barchas |
| 4,795,421 A | 1/1989 | Blasius, Jr. et al. |
| 4,811,734 A | 3/1989 | McGurk-Burleson et al. |
| 4,836,192 A | 6/1989 | Abbate |
| 4,875,287 A | 10/1989 | Creasy et al. |
| 4,886,078 A | 12/1989 | Shiffman |
| 4,887,994 A | 12/1989 | Bedford |
| 4,900,316 A | 2/1990 | Yamamoto |
| 4,917,086 A | 4/1990 | Feltovich et al. |
| 4,925,450 A | 5/1990 | Imonti et al. |
| 4,940,350 A | 7/1990 | Kim |
| 4,957,747 A | 9/1990 | Stiefel |
| 5,006,004 A | 4/1991 | Dirksing et al. |
| 5,006,339 A | 4/1991 | Bargery et al. |
| 5,012,797 A | 5/1991 | Liang et al. |
| 5,035,089 A | 7/1991 | Tillman et al. |
| 5,037,431 A | 8/1991 | Summers et al. |
| 5,037,432 A | 8/1991 | Molinari |
| 5,054,339 A | 10/1991 | Yacowitz |
| 5,100,412 A | 3/1992 | Rosso |
| 5,100,424 A | 3/1992 | Jang |
| 5,119,839 A | 6/1992 | Rudolph |
| 5,122,153 A | 6/1992 | Harrel |
| 5,171,215 A | 12/1992 | Flanagan |
| 5,192,269 A | 3/1993 | Poli et al. |
| 5,207,234 A | 5/1993 | Rosso |
| 5,222,956 A | 6/1993 | Waldron |
| 5,242,433 A | 9/1993 | Smith et al. |
| 5,254,109 A | 10/1993 | Smith et al. |
| 5,368,581 A | 11/1994 | Smith et al. |
| 5,387,215 A | 2/1995 | Fisher |
| 5,391,151 A | 2/1995 | Wilmot |
| 5,417,674 A | 5/1995 | Smith et al. |
| 5,419,772 A | 5/1995 | Teitz et al. |
| 5,441,490 A | 8/1995 | Svedman |
| 5,460,620 A | 10/1995 | Smith et al. |
| 5,470,323 A | 11/1995 | Smith et al. |
| 5,484,427 A | 1/1996 | Gibbons |
| 5,490,736 A | 2/1996 | Haber et al. |
| 5,512,044 A | 4/1996 | Duer |
| 5,562,642 A | 10/1996 | Smith et al. |
| 5,562,643 A | 10/1996 | Johnson |
| 5,611,687 A | 3/1997 | Wagner |
| 5,612,797 A | 3/1997 | Clarke |
| 5,674,235 A | 10/1997 | Parisi |
| 5,676,643 A | 10/1997 | Cann et al. |
| 5,676,648 A | 10/1997 | Henley |
| 5,683,971 A | 11/1997 | Rose et al. |
| 5,697,920 A | 12/1997 | Gibbons |
| 5,707,383 A | 1/1998 | Bays |
| 5,713,785 A | 2/1998 | Nishio |
| 5,735,833 A | 4/1998 | Olson |
| 5,759,185 A | 6/1998 | Grinberg |
| 5,762,640 A | 6/1998 | Kajiwara et al. |
| 5,779,519 A | 7/1998 | Oliver |
| 5,800,446 A | 9/1998 | Banuchi |
| 5,807,353 A | 9/1998 | Schmitz |
| 5,810,842 A | 9/1998 | Di Fiore et al. |
| 5,813,416 A | 9/1998 | Rudolph |
| 5,817,050 A | 10/1998 | Klein |
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,882,201 A | 3/1999 | Salem |
| 5,885,260 A | 3/1999 | Mehl, Sr. et al. |
| 5,908,401 A | 6/1999 | Henley |
| 5,919,152 A | 7/1999 | Zygmont |

(56) References Cited

U.S. PATENT DOCUMENTS

| | | |
|---|---|---|
| 5,954,730 A | 9/1999 | Bernabei |
| 5,971,999 A | 10/1999 | Naldoni |
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,090,085 A | 7/2000 | Mehl, Sr. et al. |
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Parkin et al. |
| 6,183,451 B1 | 2/2001 | Mehl, Sr. et al. |
| 6,183,483 B1 | 2/2001 | Chang |
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,264,666 B1 | 7/2001 | Coleman et al. |
| 6,277,128 B1 * | 8/2001 | Muldner .............. A61B 17/545 606/131 |
| 6,283,978 B1 | 9/2001 | Cheski et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bernabei et al. |
| 6,332,886 B1 | 12/2001 | Green et al. |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,511,486 B2 | 1/2003 | Mercier et al. |
| 6,514,262 B1 | 2/2003 | Di Fiore et al. |
| 6,527,783 B1 | 3/2003 | Ignon |
| 6,535,761 B2 | 3/2003 | Bernabei |
| 6,540,757 B1 | 4/2003 | Hruska et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B2 | 7/2003 | Garcia |
| 6,592,595 B1 | 7/2003 | Mallett et al. |
| 6,629,983 B1 | 10/2003 | Ignon |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| 6,685,853 B1 | 2/2004 | Angelopoulous et al. |
| 6,687,537 B2 | 2/2004 | Bernabei |
| 6,695,853 B2 | 2/2004 | Karasiuk |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| 6,800,083 B2 | 10/2004 | Hiblar et al. |
| 6,869,611 B1 | 3/2005 | Kligman et al. |
| 6,905,487 B2 | 6/2005 | Zimmerman |
| 6,911,031 B2 | 6/2005 | Muldner |
| 6,926,681 B1 | 8/2005 | Ramey et al. |
| 6,942,649 B2 | 9/2005 | Ignon et al. |
| 6,960,206 B2 | 11/2005 | Keane |
| 7,001,355 B2 | 2/2006 | Nunomura et al. |
| 7,004,933 B2 | 2/2006 | McDaniel |
| 7,044,938 B2 | 5/2006 | La Bianco et al. |
| 7,052,503 B2 | 5/2006 | Bernabei |
| 7,069,073 B2 | 6/2006 | Henley et al. |
| 7,070,488 B2 | 7/2006 | Suissa et al. |
| 7,083,580 B2 | 8/2006 | Bernabei |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| 7,276,051 B1 | 10/2007 | Henley et al. |
| 7,293,930 B2 | 11/2007 | Chuang |
| 7,314,326 B2 | 1/2008 | Rosenberg |
| 7,316,657 B2 | 1/2008 | Kleinhenz et al. |
| 7,318,828 B2 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,427,273 B2 | 9/2008 | Mitsui |
| 7,458,944 B2 | 12/2008 | Liste et al. |
| 7,476,205 B2 | 1/2009 | Erdmann |
| 7,477,938 B2 | 1/2009 | Sun et al. |
| 7,482,314 B2 | 1/2009 | Grimes et al. |
| 7,485,125 B2 | 2/2009 | Sjostrom |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,901,373 B2 | 3/2011 | Tavger |
| 7,951,156 B2 | 5/2011 | Karasiuk |
| 7,993,333 B2 | 8/2011 | Oral et al. |
| 8,025,669 B1 | 9/2011 | David et al. |
| RE42,960 E | 11/2011 | Waldron |
| 8,048,089 B2 * | 11/2011 | Ignon .................. A61B 17/545 606/131 |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| 8,221,437 B2 | 7/2012 | Waldron et al. |
| 8,236,008 B2 | 8/2012 | Boone, III et al. |
| 8,277,287 B2 | 10/2012 | Hart |
| 8,337,513 B2 | 12/2012 | Shadduck |
| 8,343,116 B2 | 1/2013 | Ignon et al. |
| 8,814,836 B2 | 8/2014 | Ignon et al. |
| 9,056,193 B2 | 6/2015 | Ignon et al. |
| 9,468,464 B2 | 10/2016 | Shadduck |

(56) References Cited

U.S. PATENT DOCUMENTS

| | | |
|---|---|---|
| 9,474,886 B2 | 10/2016 | Ignon et al. |
| 9,486,615 B2 | 11/2016 | Ignon et al. |
| 9,498,610 B2 | 11/2016 | Ignon et al. |
| 9,550,052 B2 | 1/2017 | Ignon et al. |
| 9,566,088 B2 | 2/2017 | Ignon et al. |
| 9,642,997 B2 | 5/2017 | Ignon et al. |
| 9,662,482 B2 | 5/2017 | Ignon et al. |
| 9,775,646 B2 | 10/2017 | Shadduck |
| 9,814,868 B2 | 11/2017 | Ignon et al. |
| 10,035,007 B2 | 7/2018 | Ignon et al. |
| 10,172,644 B2 | 1/2019 | Ignon et al. |
| 10,179,229 B2 | 1/2019 | Ignon et al. |
| 2001/0023351 A1 | 9/2001 | Eilers |
| 2001/0037118 A1* | 11/2001 | Shadduck ............ A61B 17/545 606/131 |
| 2001/0049511 A1 | 12/2001 | Coleman et al. |
| 2002/0016601 A1 | 2/2002 | Shadduck |
| 2002/0041891 A1 | 4/2002 | Cheski |
| 2002/0058952 A1 | 5/2002 | Weber et al. |
| 2002/0107527 A1 | 8/2002 | Burres |
| 2002/0128663 A1 | 9/2002 | Mercier et al. |
| 2002/0133110 A1 | 9/2002 | Citow |
| 2002/0133176 A1 | 9/2002 | Parkin et al. |
| 2002/0151826 A1 | 10/2002 | Ramey et al. |
| 2002/0151908 A1 | 10/2002 | Mallett, Sr. et al. |
| 2002/0188261 A1 | 12/2002 | Hruska |
| 2003/0012415 A1 | 1/2003 | Cossel |
| 2003/0018252 A1 | 1/2003 | Duchon et al. |
| 2003/0060834 A1 | 3/2003 | Muldner |
| 2003/0093040 A1 | 5/2003 | Mikszta et al. |
| 2003/0093089 A1 | 5/2003 | Greenberg |
| 2003/0097139 A1 | 5/2003 | Karasiuk |
| 2003/0167032 A1 | 9/2003 | Ignon |
| 2003/0187462 A1 | 10/2003 | Chang |
| 2003/0208159 A1 | 11/2003 | Ignon et al. |
| 2003/0212127 A1 | 11/2003 | Glassman et al. |
| 2003/0212415 A1 | 11/2003 | Karasiuk |
| 2004/0010222 A1 | 1/2004 | Nunomura et al. |
| 2004/0010269 A1 | 1/2004 | Grimes et al. |
| 2004/0015139 A1 | 1/2004 | La Bianco |
| 2004/0087972 A1 | 5/2004 | Mulholland et al. |
| 2004/0092895 A1 | 5/2004 | Harmon |
| 2004/0092959 A1 | 5/2004 | Bernaz |
| 2004/0097967 A1 | 5/2004 | Ignon |
| 2004/0122447 A1 | 6/2004 | Harmon et al. |
| 2004/0127914 A1 | 7/2004 | Chung |
| 2004/0143274 A1 | 7/2004 | Shadduck |
| 2004/0162565 A1 | 8/2004 | Carson et al. |
| 2004/0166172 A1 | 8/2004 | Rosati et al. |
| 2004/0219179 A1 | 11/2004 | McDaniel |
| 2004/0236291 A1 | 11/2004 | Zelickson et al. |
| 2004/0243149 A1 | 12/2004 | Lee, Jr. |
| 2004/0254587 A1 | 12/2004 | Park |
| 2004/0267285 A1 | 12/2004 | Chang |
| 2005/0037034 A1 | 2/2005 | Rhoades |
| 2005/0038448 A1 | 2/2005 | Chung |
| 2005/0059940 A1 | 3/2005 | Weber et al. |
| 2005/0084509 A1 | 4/2005 | Bernstein |
| 2005/0148958 A1 | 7/2005 | Rucinski |
| 2005/0203111 A1 | 9/2005 | David |
| 2005/0209611 A1 | 9/2005 | Greenberg |
| 2005/0283176 A1 | 12/2005 | Law |
| 2006/0002960 A1 | 1/2006 | Zoeteweij et al. |
| 2006/0116674 A1 | 6/2006 | Goble et al. |
| 2006/0161178 A1 | 7/2006 | Lee |
| 2006/0189964 A1 | 8/2006 | Anderson |
| 2006/0191562 A1 | 8/2006 | Numomura |
| 2006/0200099 A1 | 9/2006 | La Bianco et al. |
| 2006/0200172 A1 | 9/2006 | Shadduck |
| 2006/0200173 A1 | 9/2006 | Shadduck |
| 2006/0212029 A1 | 9/2006 | Villacampa et al. |
| 2006/0222445 A1 | 10/2006 | Chuang |
| 2006/0253125 A1 | 11/2006 | Ignon |
| 2006/0264893 A1 | 11/2006 | Sage, Jr. et al. |
| 2007/0005078 A1 | 1/2007 | Hart et al. |
| 2007/0043382 A1 | 2/2007 | Cheney |
| 2007/0065515 A1 | 3/2007 | Key |
| 2007/0088371 A1 | 4/2007 | Karasiuk |
| 2007/0123808 A1 | 5/2007 | Rhoades |
| 2007/0154502 A1 | 7/2007 | Hattendorf et al. |
| 2007/0156124 A1 | 7/2007 | Ignon et al. |
| 2007/0178121 A1 | 8/2007 | First et al. |
| 2007/0198031 A1 | 8/2007 | Kellogg |
| 2007/0208353 A1 | 9/2007 | Shadduck |
| 2007/0239173 A1 | 10/2007 | Khalaj |
| 2008/0027328 A1 | 1/2008 | Klopotek et al. |
| 2008/0091179 A1 | 4/2008 | Durkin et al. |
| 2008/0103563 A1 | 5/2008 | Powell |
| 2008/0119781 A1 | 5/2008 | King |
| 2008/0132914 A1 | 6/2008 | Bossard et al. |
| 2008/0139974 A1 | 6/2008 | Da Silva |
| 2008/0154161 A1 | 6/2008 | Abbott |
| 2008/0193493 A1 | 8/2008 | Rhoades |
| 2008/0200861 A1 | 8/2008 | Shalev et al. |
| 2008/0208146 A1 | 8/2008 | Brandwein et al. |
| 2008/0214987 A1 | 9/2008 | Xu |
| 2008/0215068 A1 | 9/2008 | Hart et al. |
| 2008/0221548 A1 | 9/2008 | Danenberg et al. |
| 2008/0243039 A1 | 10/2008 | Rhoades |
| 2008/0287864 A1 | 11/2008 | Rosenberg |
| 2008/0300529 A1 | 12/2008 | Reinstein |
| 2008/0300552 A1 | 12/2008 | Cichocki et al. |
| 2009/0048557 A1 | 2/2009 | Yeshurun et al. |
| 2009/0053390 A1 | 2/2009 | Sakou et al. |
| 2009/0062815 A1 | 3/2009 | Karasiuk et al. |
| 2009/0099091 A1 | 4/2009 | Hantash |
| 2009/0099093 A1 | 4/2009 | Hantash |
| 2009/0124985 A1 | 5/2009 | Hasenoehrl et al. |
| 2009/0138026 A1 | 5/2009 | Wu |
| 2009/0177171 A1 | 7/2009 | Ignon et al. |
| 2009/0192442 A1 | 7/2009 | Ignon et al. |
| 2009/0222023 A1 | 9/2009 | Boone, III et al. |
| 2010/0045427 A1 | 2/2010 | Boone, III et al. |
| 2010/0049177 A1 | 2/2010 | Boone, III et al. |
| 2010/0049210 A1 | 2/2010 | Boone, III et al. |
| 2010/0217357 A1 | 8/2010 | Da Silva |
| 2010/0305495 A1 | 12/2010 | Anderson et al. |
| 2011/0054490 A1 | 3/2011 | Hart |
| 2011/0066162 A1 | 3/2011 | Cohen |
| 2011/0082415 A1 | 4/2011 | Ignon et al. |
| 2012/0022435 A1 | 1/2012 | Ignon et al. |
| 2012/0041338 A1 | 2/2012 | Chickering, III et al. |
| 2012/0136374 A1 | 5/2012 | Karasiuk |
| 2013/0004230 A1 | 1/2013 | Kirk, III et al. |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144280 A1 | 6/2013 | Eckhouse et al. |
| 2013/0158547 A1 | 6/2013 | David |
| 2014/0343481 A1 | 11/2014 | Ignon |
| 2014/0343574 A1 | 11/2014 | Ignon et al. |
| 2015/0032047 A1 | 1/2015 | Ignon et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272623 A1 | 10/2015 | Ignon et al. |
| 2015/0290442 A1 | 10/2015 | Ignon et al. |
| 2016/0038183 A1 | 2/2016 | Ignon et al. |
| 2016/0256671 A1 | 9/2016 | Ignon et al. |
| 2017/0036002 A1 | 2/2017 | Ignon et al. |
| 2017/0065801 A1 | 3/2017 | Ignon et al. |
| 2017/0209894 A1 | 7/2017 | Sporrer |
| 2017/0224972 A1 | 8/2017 | Ignon et al. |
| 2017/0245876 A1 | 8/2017 | Ignon et al. |
| 2017/0266424 A1 | 9/2017 | Ignon et al. |
| 2017/0319836 A1 | 11/2017 | Ignon et al. |

(56) References Cited

U.S. PATENT DOCUMENTS

| | | | |
|---|---|---|---|
| 2017/0333689 | A1 | 11/2017 | Ignon et al. |
| 2018/0318568 | A1 | 11/2018 | Ignon et al. |

FOREIGN PATENT DOCUMENTS

| | | |
|---|---|---|
| CA | 2 340 154 | 9/2002 |
| DE | 59 95 21 | 7/1934 |
| DE | 24 15 633 | 10/1975 |
| DE | 33 38 057 | 8/1984 |
| DE | 34 21 390 | 12/1985 |
| DE | 234 608 | 4/1986 |
| DE | 35 03 343 | 8/1986 |
| DE | 83 30 191 | 6/1987 |
| DE | 37 40 902 | 12/1988 |
| DE | 42 37 940 | 5/1993 |
| DE | 298 08 395 | 8/1998 |
| DE | 10 2004 015815 | 11/2005 |
| EP | 0 258 901 | 9/1987 |
| EP | 0 564 392 | 3/1993 |
| EP | 0 784 997 | 7/1997 |
| EP | 2106780 | 3/2016 |
| ES | 1 037 776 | 4/1998 |
| FR | 2 712 172 | 5/1995 |
| FR | 2 773 461 | 7/1999 |
| GB | 1 372 609 | 10/1974 |
| GB | 2306351 | 5/1997 |
| IT | 553 076 | 12/1956 |
| IT | 118 49 22 | 3/1985 |
| JP | H05-042060 | 2/1993 |
| JP | 1993-088552 | 12/1993 |
| JP | 1997-294747 | 11/1997 |
| JP | 2003-534881 | 11/2003 |
| JP | 2003-339713 | 12/2003 |
| JP | 2004-275721 | 10/2004 |
| JP | 2006-503627 | 2/2006 |
| JP | 2006-204767 | 10/2006 |
| KR | 20-0280320 | 7/2002 |
| KR | 10-20070070173 | 7/2007 |
| WO | WO 1994/024980 | 11/1994 |
| WO | WO 1997/011650 | 3/1997 |
| WO | WO 2000/015300 | 3/2000 |
| WO | WO 2001/93931 | 12/2001 |
| WO | WO 2003/073917 | 9/2003 |
| WO | WO 2004/037098 | 5/2004 |
| WO | WO 2005/070313 | 8/2005 |
| WO | WO 2006/018731 | 2/2006 |
| WO | WO 2006/031413 | 3/2006 |
| WO | WO 2007/114904 | 10/2007 |
| WO | WO 2009/088884 | 7/2009 |
| WO | WO 2009/097451 | 8/2009 |
| WO | WO 2012/145667 | 10/2012 |
| WO | WO 2014/151104 | 9/2014 |
| WO | WO 2016/106396 | 6/2016 |
| WO | WO 2017/007939 | 1/2017 |

OTHER PUBLICATIONS

Cox III et al., Decreased Splatter in Dermabrasion, Arch Facial Plastic Surgery, Jan.-Mar. 2000, vol. 2, pp. 23-26.

Ditre et al., Effect of α-hydroxy acids on photoaged skin: A pilot clinical, histologic, and ultrastructural study, Journal of American Academy of Dermatology, Feb. 1996, vol. 34, No. 2, Part 1, pp. 187-195.

Harris et al., Combining Manual Dermasanding with Low Strength Trichloroacetic Acid to Improve Antinically Injured Skin, The Journal of Dermatologic Surgery and Oncology, Jul. 1994, vol. 20, No. 7, pp. 436-442.

Microdermabrader Pepita Instruction Manual, Mattioli Engineering S.R.L., PEP_USA2.doc Rev 1.1, Sep. 29, 1997.

* cited by examiner

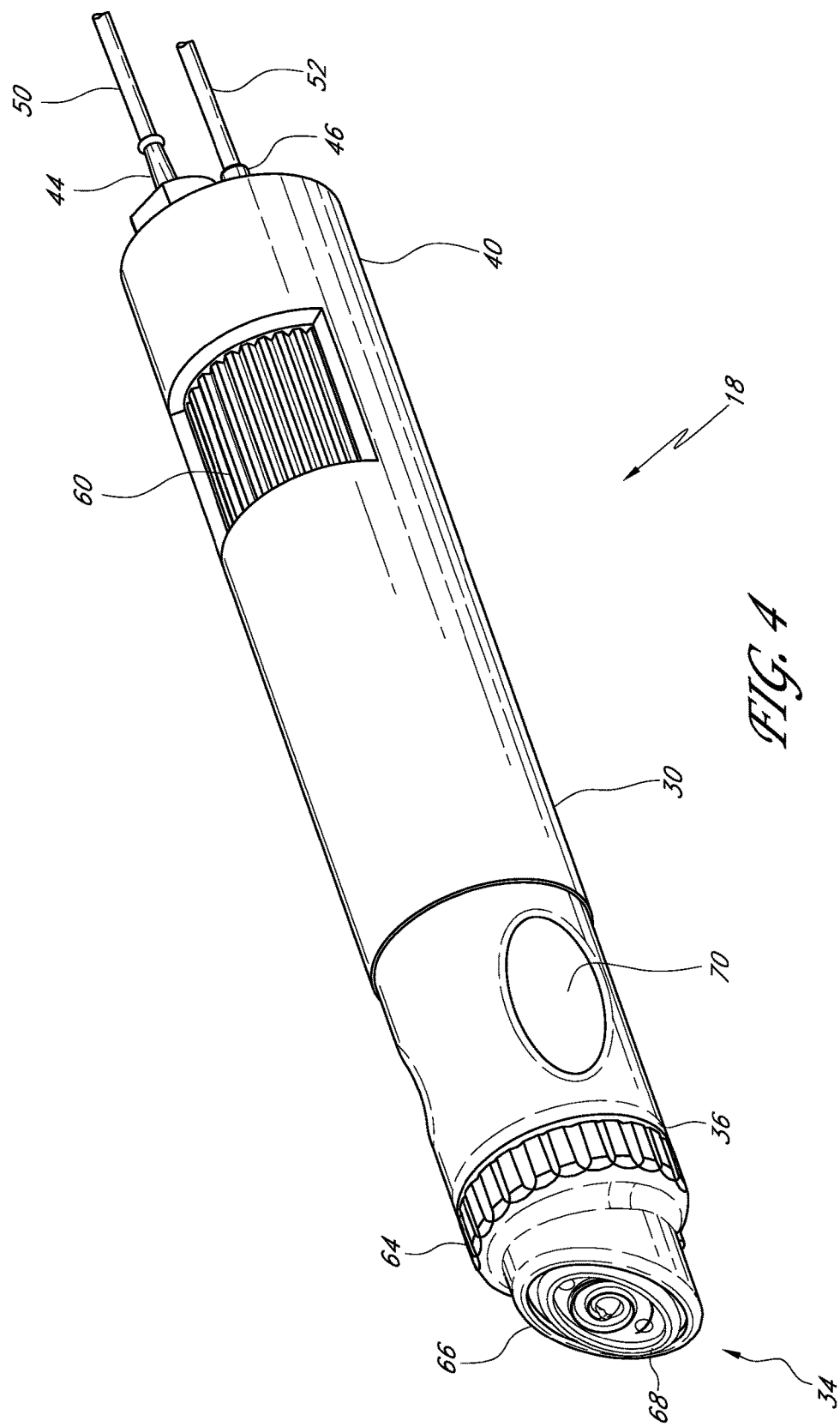

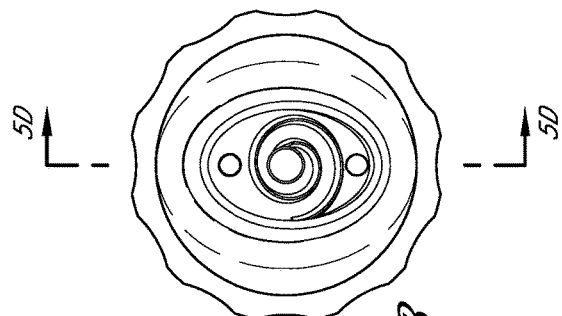
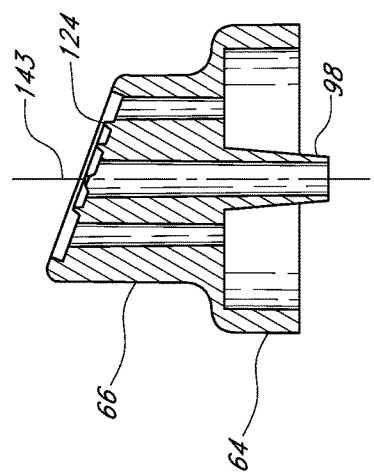
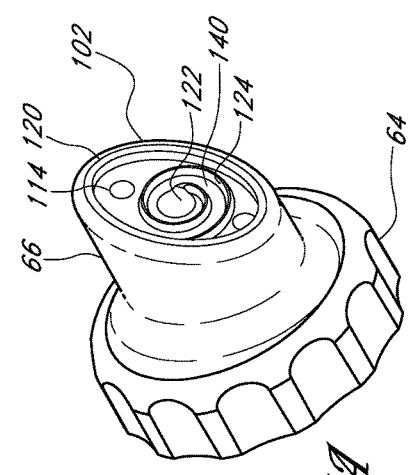
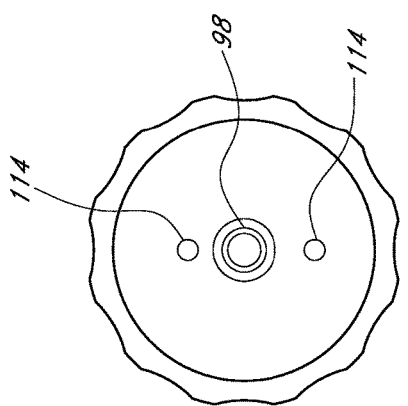

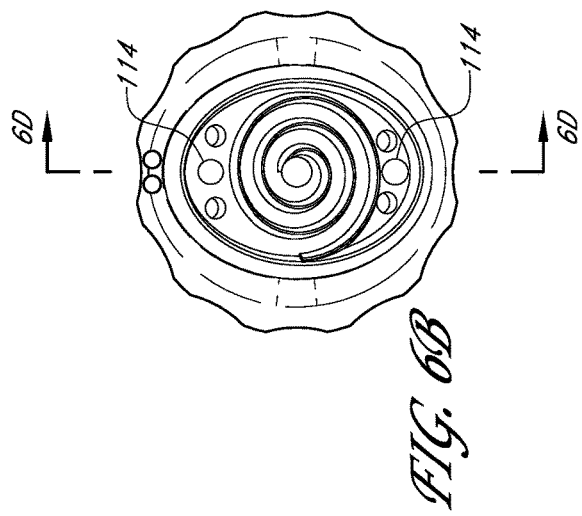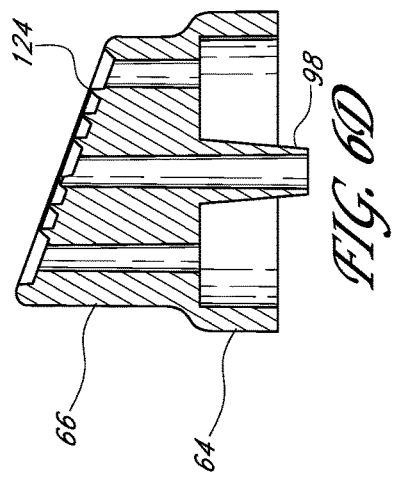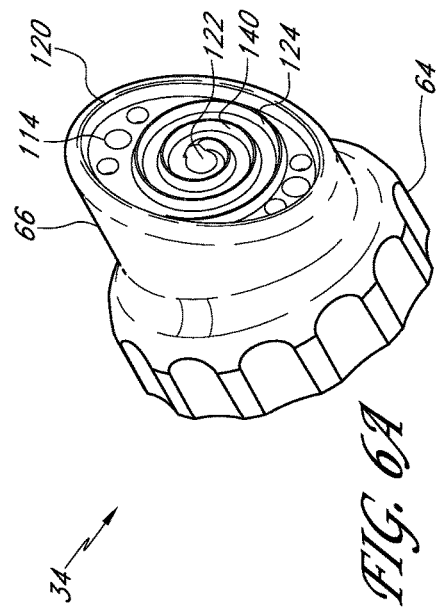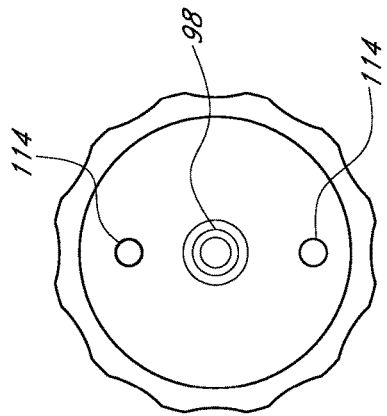

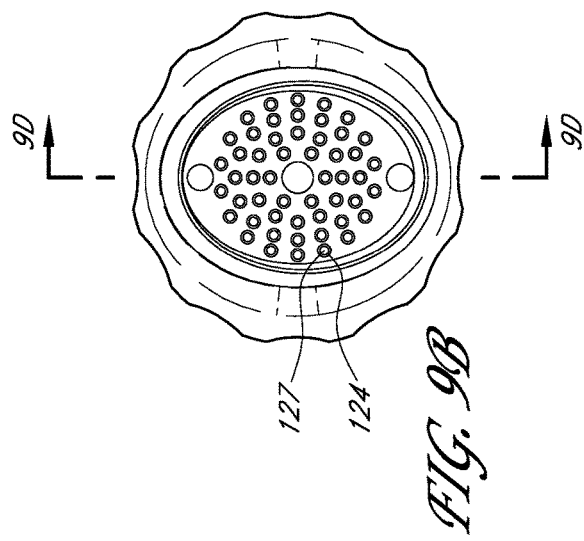
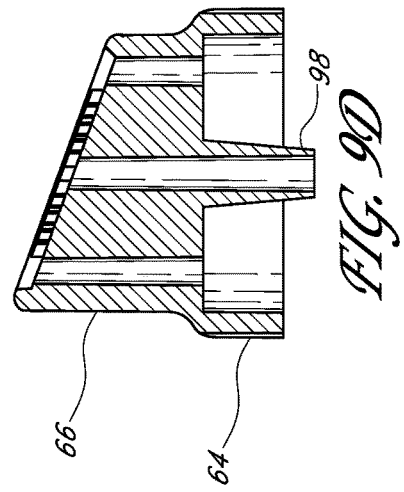
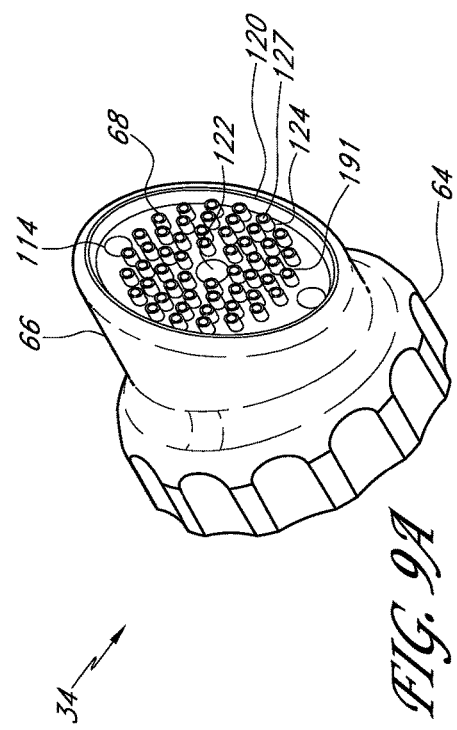
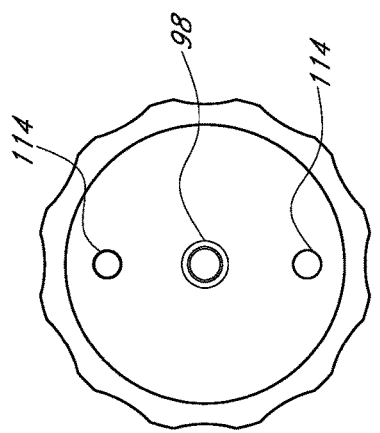

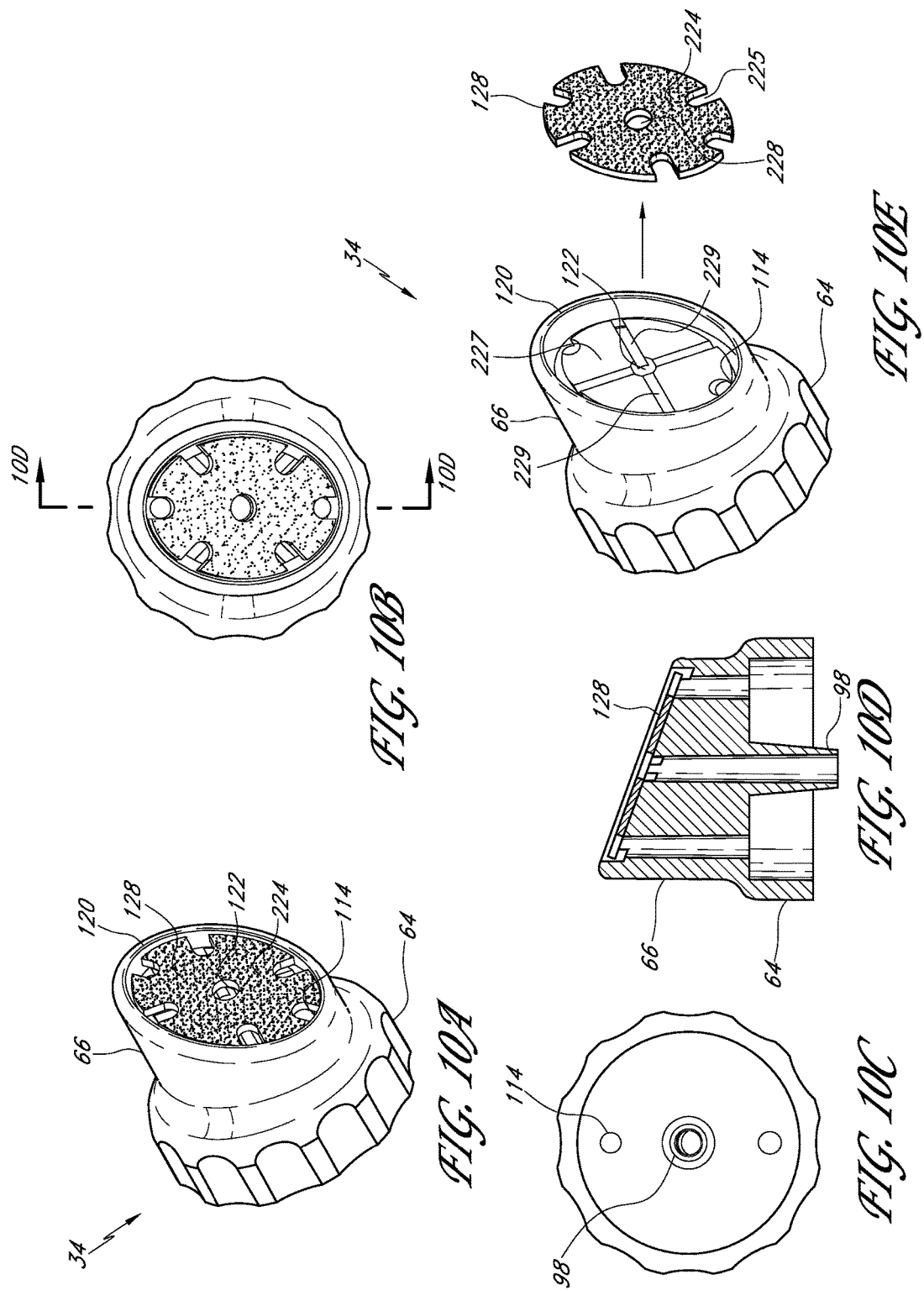

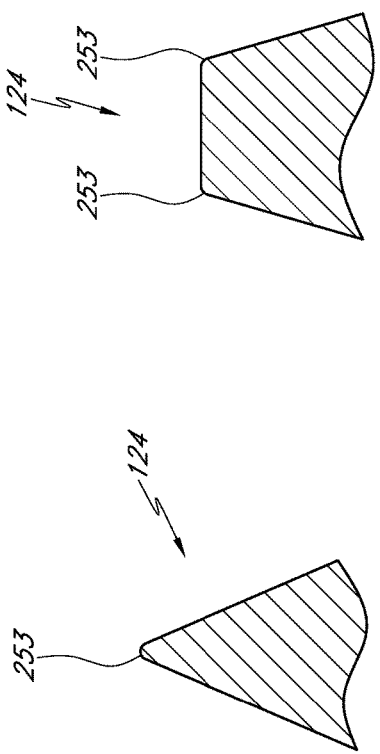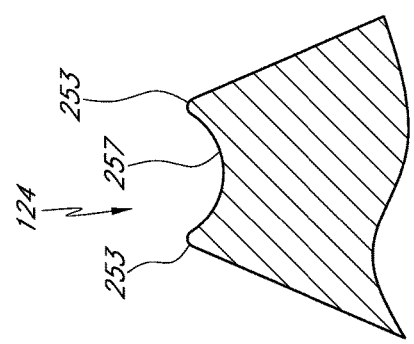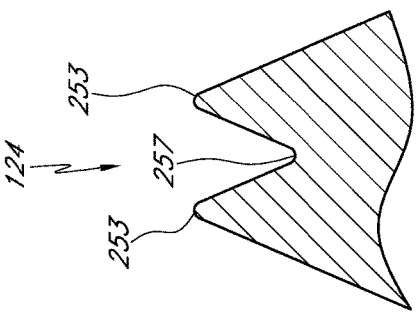

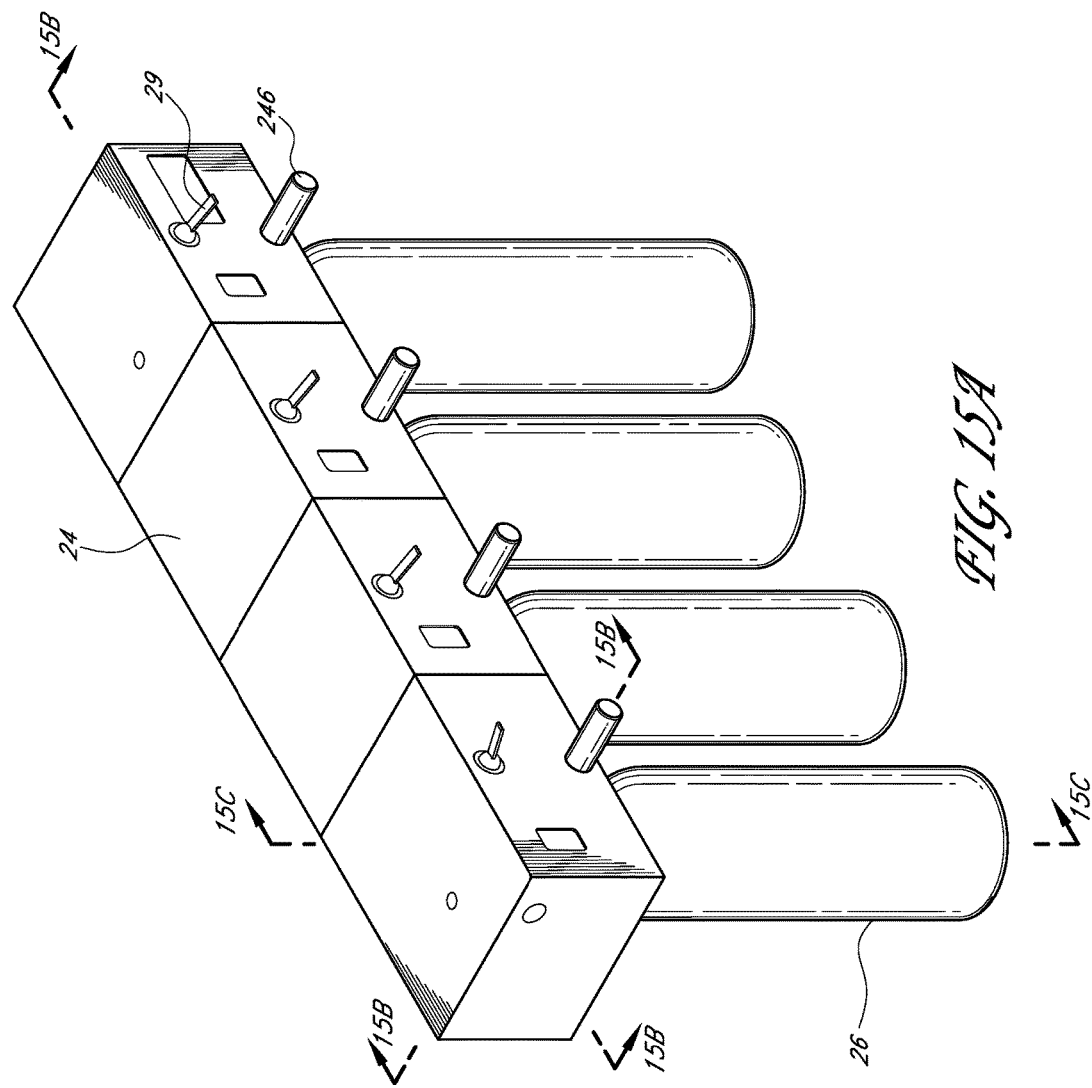

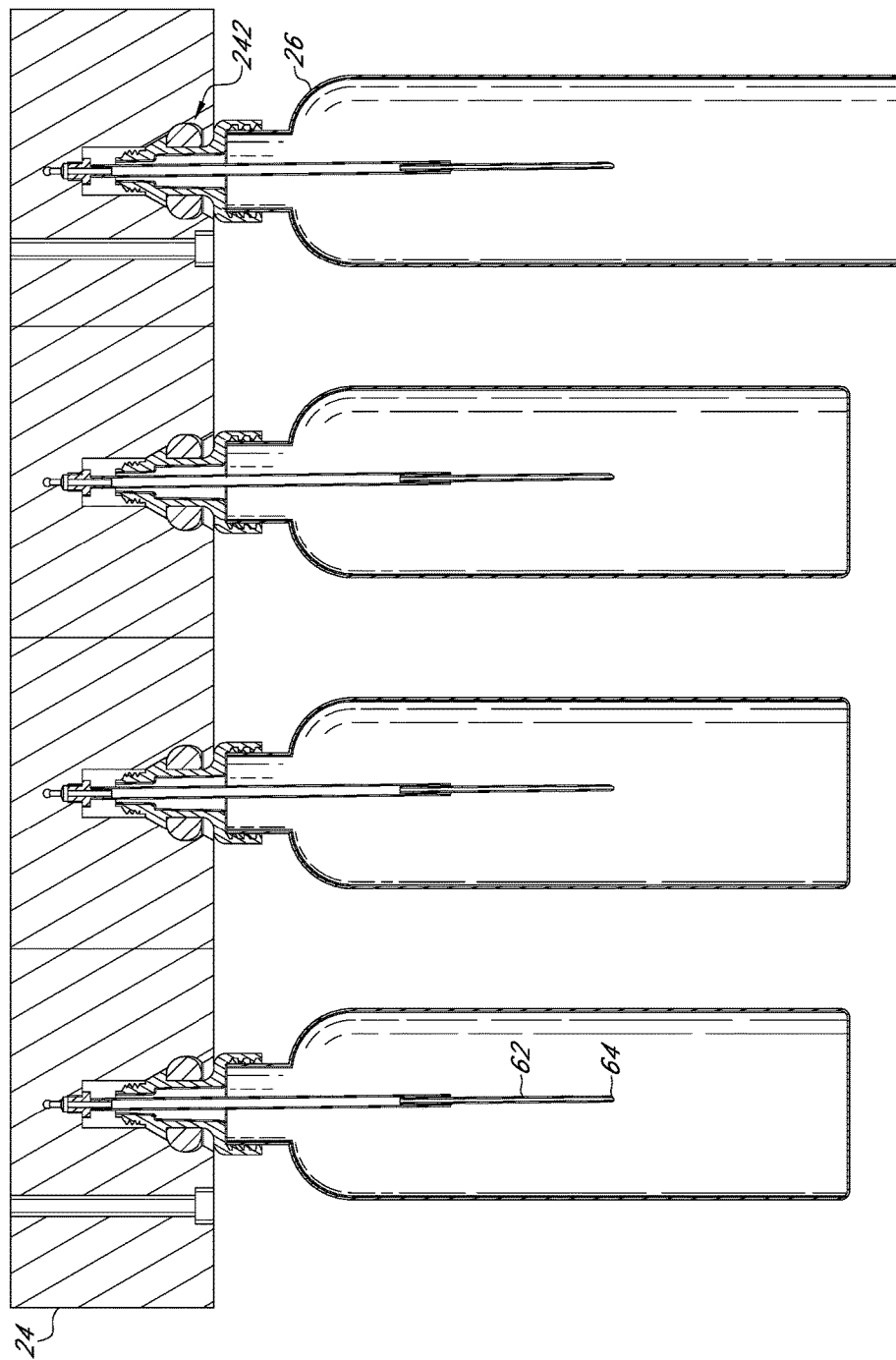

TIPS FOR SKIN TREATMENT DEVICE

CROSS-REFERENCE TO RELATED APPLICATIONS

This is a continuation of U.S. patent application Ser. No. 14/700,789 filed Apr. 30, 2015, which is a continuation of U.S. patent application Ser. No. 13/267,554 filed Oct. 6, 2011 and issued as U.S. Pat. No. 9,474,886, which is a continuation of U.S. patent application Ser. No. 11/392,348 filed Mar. 29, 2006 and issued as U.S. Pat. No. 8,048,089, which claims the benefit of U.S. Provisional Application No. 60/755,310 filed Dec. 30, 2005 and U.S. Provisional Application No. 60/764,668 filed Feb. 2, 2006. The entireties of all of the aforementioned applications are hereby incorporated by reference herein.

BACKGROUND

Field

The invention relates in general to the field of skin treatment, and more specifically to apparatuses and methods for treating a person's skin.

Description of the Related Art

Abrasion of the outer layer or epidermis of the skin is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin.

Dermabrasion refers to a procedure in which the surface of the skin is removed due to mechanical rubbing by a handpiece with an abrasive element that is often in the form of a burr, wheel, or disc. This process tends to be painful and messy. In fact, the procedure is sometimes painful enough to require a local anesthetic. Dermabrasion leaves the skin red and raw-looking. The removed skin can take several months to regrow and heal. Recent efforts have led to the use of lasers instead of abrasive elements, which have resulted in less bleeding, but the pain and mess remains.

Efforts have been made to decrease the mess caused by the process waste, such as removed skin and blood, by adding a suction element. As the process waste is drawn into the suction opening, skin that has not been removed is also pulled against the grit surrounding the suction opening, so the procedure remains fairly messy due to the abrasion that takes place outside of the handpiece by the grit.

Microdermabrasion refers generally to a procedure in which the surface of the skin is removed due to mechanical rubbing by a handpiece emitting a stream of sand or grit. For example, a handpiece can be used to direct an air flow containing tiny crystals of aluminum oxide, sodium chloride, or sodium bicarbonate. The momentum of the grit tends to wear away two to three cell layers of the skin with each pass of the handpiece. Alternatively, new "crystal-free" microdermabrasion techniques utilize a diamond-tipped handpiece without a stream of grit.

Efforts to add a suction element have been more successful in microdermabrasion than in dermabrasion because the handpiece applying the stream of grit is more controllable to a localized area. That is, as the removed skin is drawn into the suction opening, skin that has not been removed is also pulled towards the handpiece where it is treated with the grit stream, allowing for simultaneous local treatment and suction.

Microdermabrasion removes moisture from the skin, so the procedure is always followed by the application of moisturizing creams. However, similar to topical application of moisturizing creams prior to microdermabrasion, the moisturizing elements only work as deep as the active ingredients can passively migrate through the remaining epidermis.

SUMMARY

In some embodiments, an apparatus for treating skin has a console with a user input device and a handpiece assembly. The handpiece assembly is configured to treat skin. A fluid line provides fluid communication between the console and the handpiece assembly. A manifold system is coupled to the console and controlled by the user input device, such as a computer, touchscreen, keyboard, and the like. The manifold system is configured to hold releasably a plurality of fluid sources and deliver fluid from at least one of the plurality of fluid sources to the handpiece assembly.

In some embodiments, a tip comprising a skirt portion is configured to couple to a handpiece for treating a target area on a patient's skin. A central body portion is coupled to the skirt portion. A first passage extends through the central body portion and is configured to receive a fluid from the handpiece. At least one second passageway extending through the central body portion and is configured to convey the fluid back into the handpiece. An inner member extends in a generally spiral fashion across at least a portion of a distal face of the central body portion. The inner member defines a channel between the first passage and the at least one second passage. When the tip is place against the skin, a chamber can be formed by the channel and the person's skin.

In some embodiments, a method of treating a target region on a patient's skin comprises providing a tip including a first aperture and at least one second aperture. At least one inner member on the surface of the tip defines at least one channel between the first aperture and the at least one second aperture. An outer member is disposed on the surface of the tip. The outer member engages the target with the tip. A treatment fluid flows distally through the first aperture region and through the at least one channel. The treatment fluid flows proximally through the at least one second aperture.

In some embodiments, a tip comprises a skirt portion configured to couple to a handpiece for treating a target on a patient's skin. A central body portion is coupled to the skirt portion and includes a mounting region substantially opposite the skirt portion. The mounting region configured to receive a pad for treating the skin. A first aperture extends through the skirt portion and the central body portion and configured to receive a fluid from the handpiece. At least one second aperture extending through the skirt portion and the central body portion and configured to convey the fluid back into the handpiece.

In some embodiments, a method of treating a target region of a patient comprises providing a tip including a first aperture, at least one second aperture, and a distal end configured to receive a pad. In some variations, the first pad is attached to the distal end. The tip is engaged with the target region.

In some embodiments, a manifold system comprises a body portion configured to receive releasably at least two bottles. The manifold is configured so that it can be coupled to a console. The console includes a handpiece for treating skin. At least one elongate member is in communication with a pump and configured to extract a fluid from one of the at least two bottles. At least one switch is configured to permit or inhibit a flow of the fluid from one of the at least two bottles through the pump. In some variations, the elongate member is dimensioned to fit within one of at least two bottles to draw fluid out of the bottle.

In some embodiments, a method of treating a target region on a patient's skin comprises engaging a tip with the patient's skin such that an effective amount of skin is removed by the tip. In some variations, the tip is a dry tip. After removing an effective amount of skin, another tip (e.g., a wet tip) engages the patient's skin such that an effective amount of skin is removed by the tip. In some variations, acid is delivered out of the wet tip to facilitate skin removal. In some variations, the wet tip includes a first aperture, at least one second aperture, at least one inner member on the surface of the tip defining at least one channel between the first aperture and the at least one second aperture, and an outer member on the surface of the tip. In some variations, treatment fluid flows outwardly along the channel. In some variations, treatment fluid flows inwardly along the channel. In some variations, the wet tip comprises an abrasive pad.

In some embodiments, a method of treating a target region on a patient's skin comprises engaging a first skin treatment tip with the patient's skin. A first material is delivered out of the first skin treatment tip to a target region. A second skin treatment tip engages the target region while the first material effectively facilitates exfoliation with the second skin treatment tip. In some variations, the first material comprises an acid, hydrator, and combination thereof. In some variations, the first skin treatment tip is configured to remove skin at a different rate than the second skin treatment tip. In some variations, the first skin treatment tip is configured to exfoliate at a higher rate than the second skin treatment tip. In some variations, material is delivered out of the second treatment tip to the target region of the patient's skin.

The apparatus for treating skin can dispense treatment material that is held in containers, such as bottles, bags, pouches, or other suitable structures for holding and storing material. These containers can be non-refillable or refillable. The treatment material can be delivered by gravity feed, pumps, or suction devices. The manifold system can be used to control fluid flow from a plurality of containers to one or more handpieces.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow.

FIG. 4 is a perspective view of another embodiment of a handpiece assembly.

FIG. 5A is a perspective view of one embodiment of a tip that can be coupled to a main body of a handpiece assembly to treat a person's skin.

FIG. 5B is a top elevational view of the tip of FIG. 5A.

FIG. 5C illustrates a bottom elevational view of the tip of FIG. 5A.

FIG. 5D is a cross-sectional view of the tip of FIG. 5B taken along the line 5D-5D.

FIG. 6A is a perspective view of a tip in accordance with another embodiment.

FIG. 6B is a top elevational view of the tip of FIG. 6A.

FIG. 6C is a bottom elevational view of the tip of FIG. 6A.

FIG. 6D is a cross-sectional view of the tip of FIG. 6B taken along the line 6D-6D.

FIG. 9A is a perspective view of still another embodiment of a tip that can be coupled to a main body of a handpiece assembly.

FIG. 9B is a top elevational view of the tip of FIG. 9A.

FIG. 9C is a bottom elevational view of the tip of FIG. 9A.

FIG. 9D is a cross-sectional view of the tip of FIG. 9B taken along the line 9D-9D.

FIG. 10A is a perspective view of another embodiment of a tip for treating a person's skin.

FIG. 10B is top elevational view of the tip of FIG. 10A.

FIG. 10C is bottom elevational view of the tip of FIG. 10A.

FIG. 10D is a cross-sectional view of the tip of FIG. 10B taken along the line 10D-10D.

FIG. 10E is a perspective exploded view of the tip of FIG. 10A, wherein a pad is spaced from a tip main body.

FIGS. 11A-11E are cross-sectional views of inner members that can be used to exfoliate skin.

FIG. 15A is a perspective view of one embodiment of a manifold system holding a plurality of bottles.

FIG. 15B is a cross-sectional view of the manifold system of FIG. 15A taken along the line 15B-15B of FIG. 15A.

DETAILED DESCRIPTION

Figure 1:
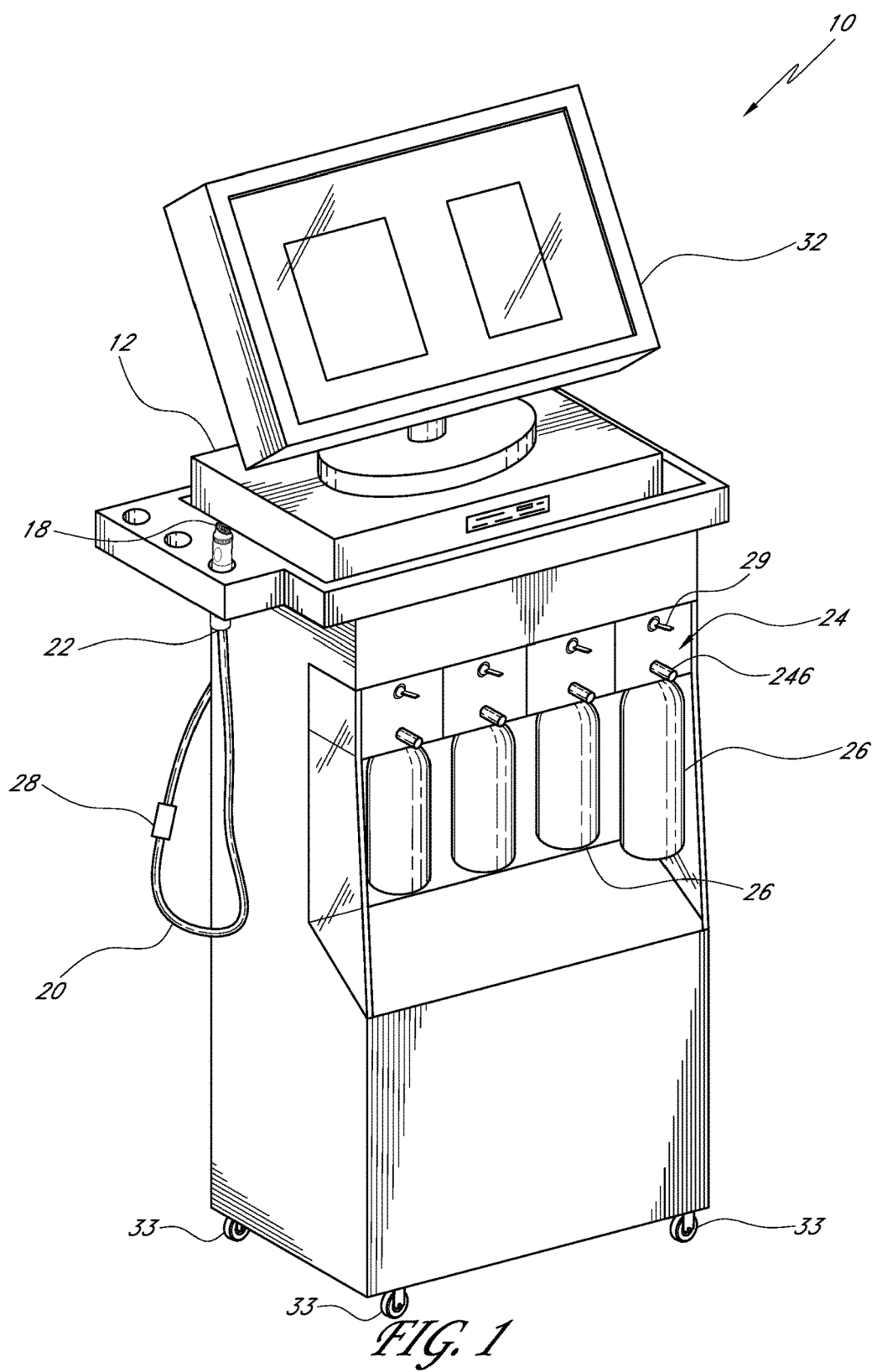
FIG. 1 is a perspective view of one embodiment of a skin treatment system.

FIG. 1 illustrates a skin treatment system 10 that can be used to perform one or more treatments on a person's skin. The illustrated skin treatment system 10 includes a console 12 and a handpiece assembly 18 connected to the console 12 via a line 20. A manifold system 24 can control the flow of treatment material from containers 26 into and through the line 20. The treatment material can be discharged out of the handpiece assembly 18 to treat a person's skin. The skin treatment system 10 can be used at a hospital, health care physicality, residences, or any other suitable location.

As explained in more detail below, the handpiece assembly 18 is applied to the target area of the patient to perform skin treatment(s). As used herein, the term "skin treatment" is a broad term and includes, but is not limited to, skin removal, skin abrasion (e.g., dermabrasion, microdermabrasion, etc.), ablating or slicing skin (preferably a thin layer of skin), stimulation (including thermal, mechanical, electrical, and/or chemical stimulation), mesotherapy, isophoresis, light therapy, vacuum therapy, and the like. Preferably, the handpiece assembly 18 administers a treatment material from at least one of the containers 26 through the line 20 to the target area of the skin while the handpiece assembly 18 engages the skin.

As used herein, the term "treatment material" is a broad term and includes, but is not limited to, medicament, a substance tending to flow or conform to the outline of its container such as fluid, gas, liquid (e.g., serums, water, saline, etc.), gel, fluidized material, additives, and/or a plurality of fine solids. The general term "fluid" is used throughout synonymously with the term "treatment material" and is to be given the same broad definition. The handpiece assembly 18 can preferably massage, abrade, ablate, or otherwise treat the target skin area while also applying a treatment material to the patient. In certain embodiments, the treatment material and tip of the handpiece 18 can work in combination for an effective and rapid skin treatment. Additionally, any number of "dry" and "wet" tips can be used alone or in combination for treatment flexibility.

With continued reference to FIG. 1 the line 20 is configured to provide fluid communication between the containers 26 and the handpiece assembly 18. The line 20 can comprise one or more conduits extending between the console 12 and the handpiece assembly 18. In certain embodiments, the line 20 includes a supply line and a waste line for delivering and returning material, respectively, as detailed below.

The distal end 22 of the line 20 is connected to the handpiece assembly 18. Preferably, the line 20 includes a filter 28 that removes contaminants or impurities from the treatment material passing through the line 20. In other embodiments, the filter 28 is located in the console 12 or the manifold system 24. The console 12 can be connected to a power source such as an AC outlet. The power source can power the handpiece assembly 18 and/or other components of the skin treatment system 10, such as, for example, pumps, valves, and the like.

In the illustrated embodiment, the console 12 comprises four casters 33 to allow for easy movement, for example, from one treatment room to another treatment room. In such an embodiment, the console 12 can be conveniently rolled on a support surface. Other means of transportation can also be employed or the console 12 can be stationary. In some embodiments, the console 12 is portable for convenient transport.

The illustrated containers 26 of FIG. 1 are preferably releasably coupled to the manifold system 24. The manifold system 24 can deliver treatment material from the containers 26 to the line 20 as mentioned above. In certain embodiments, the console 12 has a user input device 32 for selecting a treatment material to be passed through the line 20 to the handpiece assembly 18. During some skin treatment procedures, treatment materials from multiple containers 26 are sequentially or simultaneously applied to the patient's skin during a "wet" mode of operation. Alternatively, the skin treatment system 10 can be used to deliver a single treatment material to the patient's skin. In some embodiments, the console 12 can be used for a "dry" mode of operation. That is, the console 12 can be used to exfoliate skin, for example, without delivering little or substantially no treatment fluid. The skin treatment system 10 can thus provide flexibility in selecting a treatment plan.

Multiple handpieces assemblies 18 and/or tips 34 can be used during a single skin treatment procedure in a wet and/or dry mode of operation. For example, a first handpiece assembly 18 may be employed to treat a patient's face and neck while a second handpiece assembly 18 may be employed to treat other larger areas of the patient's body. Thus, different handpieces 18 can be used to treat different regions of a person's body. The configurations of the handpieces 18 and tips can be selected based on the treatment material to be applied, desired interaction with the patient's skin, size of treatment area, skin condition, and the like.

Figure 2A:
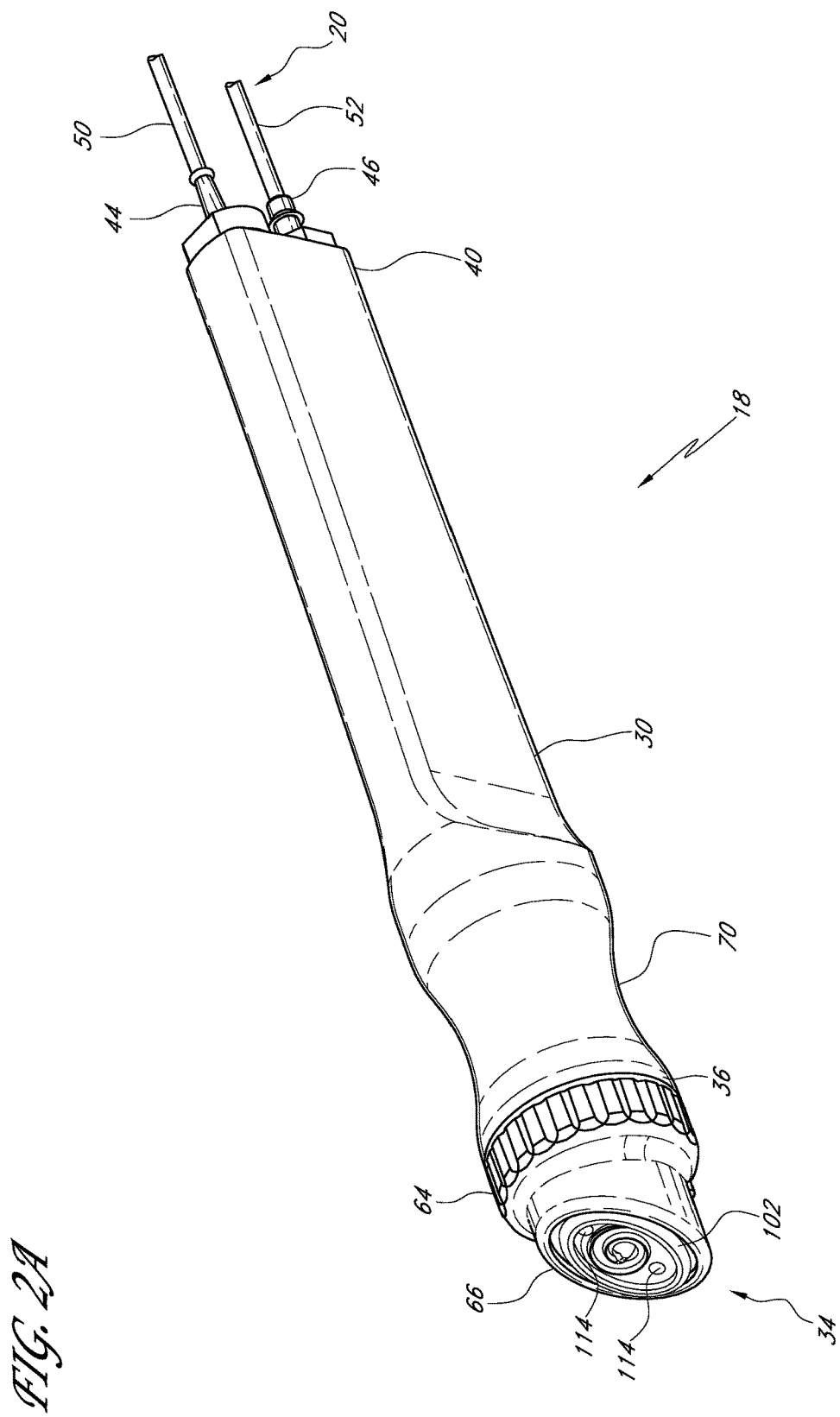
FIG. 2A is a perspective view of one embodiment of a handpiece assembly for use with the skin treatment system of FIG. 1.
Figure 2B:
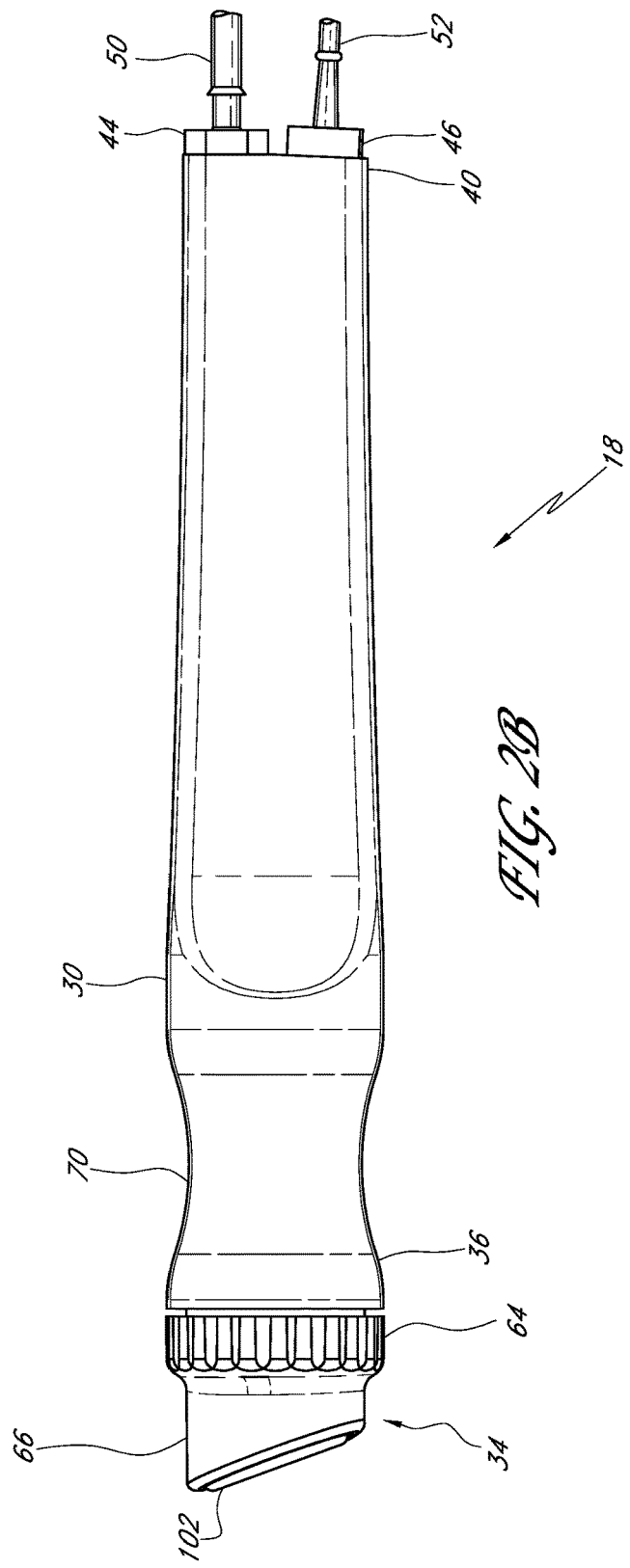
FIG. 2B is a side elevational view of the handpiece assembly of FIG. 2A.

With reference to FIGS. 2A and 2B, the handpiece assembly 18 includes a main body 30 and a tip 34. The handpiece assembly 18 can be conveniently held within the hand of a user so that the user can place the tip 34 in operative engagement with a person's skin. The user is typically an aesthetician (e.g., an aesthetician allowed to perform microdermabrasion), doctor, and other medical personnel, such as a physician assistant and nurse practitioner. In some cases, the user is the person whose skin is being treated.

The main body 30 has contoured portions 70 at its distal end 36 so that the user can comfortably grip the handpiece assembly 18 during use. The main body 30 can have other designs to provide a comfortable grip. FIG. 2A illustrates an embodiment in which the main body 30 is substantially flat on two opposing sides. FIG. 4 illustrates an embodiment in which the main body 30 is generally cylindrical.

As noted above, the tip 34 can be pressed against a patient's skin to perform a skin treatment. The distal end 102 of the tip 34 may be angled with respect to the handpiece assembly 18 to increase the contact area with the patient's skin without enlarging the handpiece assembly 18 for an ergonomic and comfortable design. The angled tip 34 can lay flat on the skin while the main body 30 is angled to the skin. The angle between the face of the distal end 102 and the longitudinal axis of the handpiece assembly 18 can be selected based on the desired size of the face of the distal end 102. In alternative embodiments, the face of the distal end 102 is generally perpendicular to the longitudinal axis of the main body 30.

The tip 34 can be permanently or temporarily coupled to the distal end 36 of the main body 30. In some embodiments, the tip 34 is disposable. As used herein, the term "disposable," when applied to a system or component (or combination of components), such as a tip, container, or pad, is a broad term and means, without limitation, that the component in question is used a finite number of times and then discarded. Some disposable components are used only once and then discarded. Other disposable components are used more than once and then discarded. In some embodiments, the tip 34 is removably coupled to the main body 30 such that the tip may be removed from the main body 30 and thrown away to avoid cross-contamination. In other embodiments, the tip 34 is a reusable tip that can be cleaned, for example by autoclaving, after each use. The tip 34 can thus be used for any number of procedures as desired.

With reference to FIGS. 2A and 2B, the proximal end 40 of the main body 30 is operatively connected to the line 20. In the embodiment illustrated, the line 20 includes an output line 50 for removing waste from the handpiece assembly 18 and an input line 52 for delivering treatment material to the handpiece assembly 18. The proximal end 40 of the main body 30 includes a plurality of connectors 44, 46, each connected to one of the conduits 50, 52. The illustrated input line 52 is connected to the connector 46, and the output line 50 is connected to the connector 44.

Figure 3:
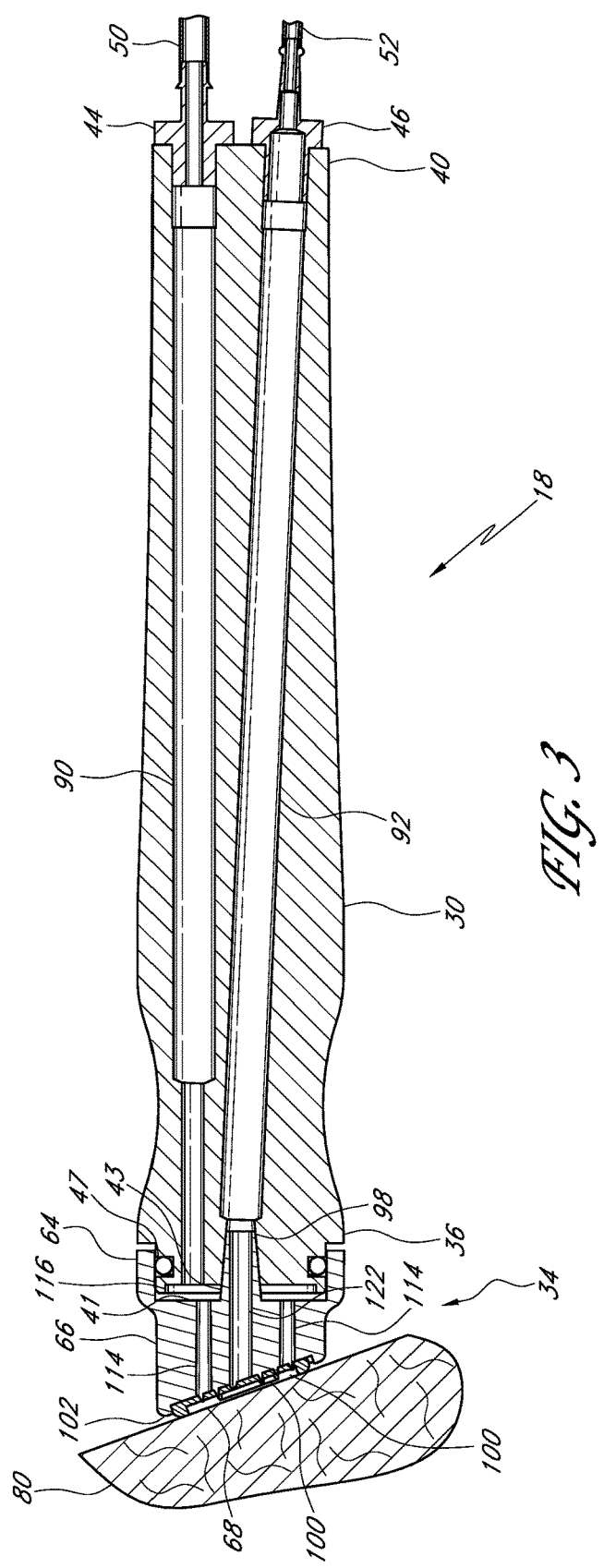
FIG. 3 is a longitudinal cross-sectional view of the handpiece assembly of FIG. 2B. The handpiece assembly is engaging a person's skin.
Figure 7B:
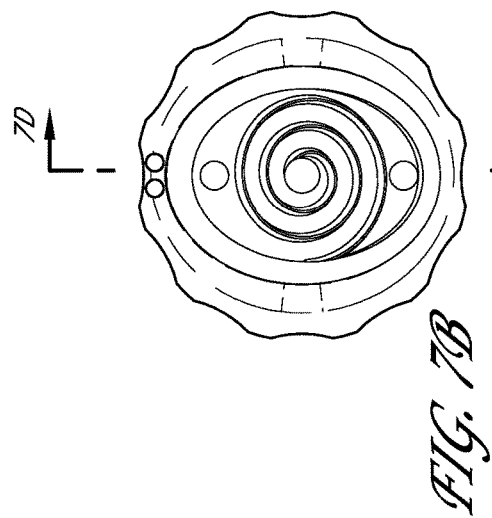
FIG. 7B is a top elevational view of the tip of FIG. 7A.
Figure 7D:
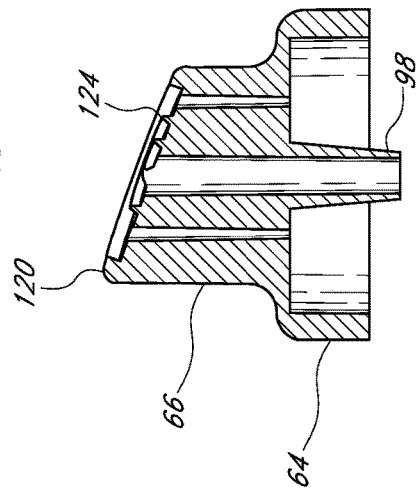
FIG. 7D is a cross-sectional view of the tip of FIG. 7B taken along the line 7D-7D.
Figure 7A:
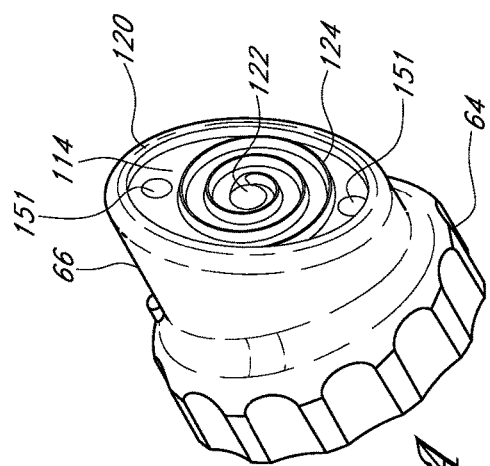
FIG. 7A is a perspective view of a tip in accordance with another embodiment.
Figure 7C:
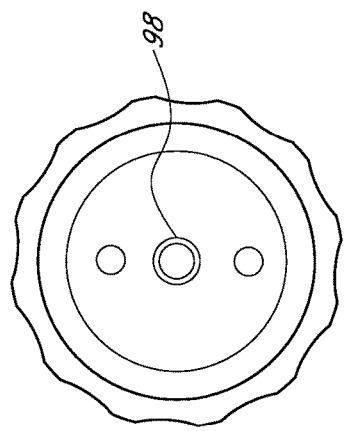
FIG. 7C is a bottom elevational view of the tip of FIG. 7A.

The input line 52 delivers treatment material from at least one of the containers 26 to the connector 46. The fluid then flows through the main body 30 and ultimately to the tip 34. As shown in FIG. 3, the main body 30 comprises a plurality of lumens 90, 92 in a fluid communication with the tip 34. Fluid from the input line 52 can flow through the input lumen 92 to the tip 34. The fluid then flows out of the tip 34 to a target skin area. The fluid is then trapped in the space 100 between the skin 80 and the tip 34. To remove the fluid, the fluid flows proximally through the lumen 90 to the output line 50. The fluid passes through the output line 50 and into the console 12. As such, fluid can continuously or intermittently flow through the handpiece assembly 18.

To treat the person's skin 80, the handpiece assembly 18 can also be moved relative to the skin 80 such that the tip 34 maintains engagement with the skin 80. The illustrated tip 34 is configured to massage the skin 80 while also providing fluid communication with the skin 80. As detailed below in connection with FIGS. 5A through 10, the tip can include sharp planing blades, blades (e.g., razor blades), raised sharp areas, molded posts, grits, or other structures for treating skin, as detailed below.

When the tip 34 and treatment material are used in combination, the handpiece assembly 18 preferably exfoliates dead skin cells and extracts impurities by applying a vacuum while simultaneously bathing the healthy underlying skin with active treatment material. The active treatment material can facilitate cleansing, exfoliating, hydrating, and/or provide residual antioxidant protection. The treatment material and tip 34, alone or in combination, can effectively and rapidly treat the target skin area. The waste material, including the used treatment material, removed skin, and/or grit, can then be drawn back through the tip 34, the main body 30 via lumen 90, and into the connector 44. The waste then flows into the output line 50 for subsequent disposal, as detailed below in connection with FIG. 4.

In some embodiments, including the illustrated embodiment of FIG. 3, the tip 34 has a tip connector 98 (see FIGS. 5C and 5D) that mates with the lumen 92. The tip 34 can provide fluid communication from the tip connector 98 to the space 100 via a through-hole 122. One or more through-holes 114 define fluid passageways through the tip 34 between the space 100 and the intermediate chamber 116.

The intermediate chamber 116 can be interposed between the through-holes 114 and the lumen 90. The intermediate chamber 116 is preferably defined by the distal face 43 of the main body 30 and the proximal face 41 of the tip 34. The intermediate chamber 116 can provide equalization of fluid between the tip 34 and the body 30. As such, a generally equal vacuum is applied to both through-holes 114. The fluid can flow through the through-holes 114, into the intermediate chamber 116, and then into the lumen 90. In some embodiments, however, the fluid flows directly from the through-holes 114 to the lumen 90 without passing through an intermediate chamber 116.

The tip 34 can have one or more sealing members to form a fluidic seal between the tip 34 and the main body 30. The illustrated main body 30 includes a sealing member 47 that engages the inner surface of the skirt 64 of the tip 34. The sealing member 47 can be a compliant member comprising rubber, polymer, plastic, or other suitable material for forming seals. In some embodiments, the sealing member 47 is an O-ring made of rubber.

With continued reference to FIG. 3, during use, treatment material can flow distally through the lumen 92 into the through-hole 122. The treatment material then proceeds through and out of the through-hole 122 into the space 180. Preferably, the treatment material spreads radially outward to the peripheral through-holes 114. The material can then flow through the through-holes 114 into the lumen 90 for subsequent removal.

In alternative embodiments, the fluid flows in the opposite direction. That is, the line 50 delivers fluid through the lumen 90 into the tip 34. The fluid flows through the intermediate chamber 116 and the through-holes 114. The fluid then flows to the chamber 100 and inwardly through the tip connector 98 to the lumen 92. The fluid proceeds proximally along the lumen 92 and ultimately into the line 52.

In yet another embodiment, the handpiece assembly 18 comprises two or more input lumens 90. Such a design allows mixing of two or more treatment materials within the handpiece assembly 18 or space 100, which would be useful for treatments with fluids that react or are unstable or degrade when stored or mixed.

As depicted in FIG. 4, the handpiece assembly 18 can optionally include a controller 60 that is configured to control the fluid flow out of the tip 34. The illustrated controller 60 can be operated to increase or decrease the flow rate of treatment fluid out of the tip 34. Alternatively or additionally, the controller 60 may control the flow rate of waste fluid flowing through the handpiece assembly 18 to the output line 50. When control of the waste treatment fluid and waste fluid is independent, the detention time of the fluid in the tip 34 may be adjusted as desired.

The illustrated controller 60 is a generally cylindrical body that is pivotally connected to the main body 30. FIG. 4 illustrates an embodiment in which the controller 60 is recessed into and partially hidden by the main body 30, although in other embodiments the controller 60 may encircle the main body 30. The controller 60 may include textured grooves to provide for easier manipulation. In some embodiments, the controller 60 is located near the distal end 36 of the handpiece assembly 18 proximal or distal of the contoured portion 70. The type and configuration of the controller 60 can be selected based on the design of the handpiece assembly 18. The controller 60 can also be a rotatable knob or handle, digital controller, and the like.

The handpiece assembly 18 can also include one or more flow rate controllers within the main body 30 that cooperate with the controller 60 to adjust the fluid flow out of the tip 34. For example, the controller 60 may comprise a flow control valve such as a globe valve, butterfly valve, needle valve, or variable orifice. Other types of flow rate controllers can also be used, such as an electrically controlled solenoid valve. In embodiments where the fluid flow is electronically controlled, the valve system may alternatively be located in the console 12 or manifold system 24. Separate devices can also be used to control the flow of treatment material. For example, clamps, pinch valves, or other suitable devices can be used to control fluid flow through the lines 50, 52.

Various types of tips 34 can be used with the handpiece assemblies 18 illustrated in FIGS. 1 to 4. FIGS. 5A through 10E illustrate embodiments, for example, of tips 34 that can be used with these handpiece assemblies 18. These tips 34 can be interchangeable to provide maximum treatment flexibility.

As shown in FIGS. 5A through 10E, the tip 34 comprises the skirt 64 and a tip main body 66 extending outwardly therefrom. The skirt 64 is preferably configured to provide a gripping surface suitable for applying leverage or force sufficient to remove the tip 34 from the main body 30. In some embodiments, the skirt 64 includes internal threads such that it can be mechanically coupled to external threads on the distal end 36 of the main body 30. In some embodiments, the tip 34 can be press fit onto the main body 30. Frictional forces can retain the tip 34 to the main body 30.

With respect to FIGS. 5A through 7, the tip 34 comprises an outer member 120 and an inner member 124. The outer member 120 preferably defines the periphery of the distal end 102 of the tip 34. When the tip 34 is placed against skin, the outer member 120 can inhibit fluid flow between the tip 34 and the skin and define the outer portion of the space 100.

Figure 8B:
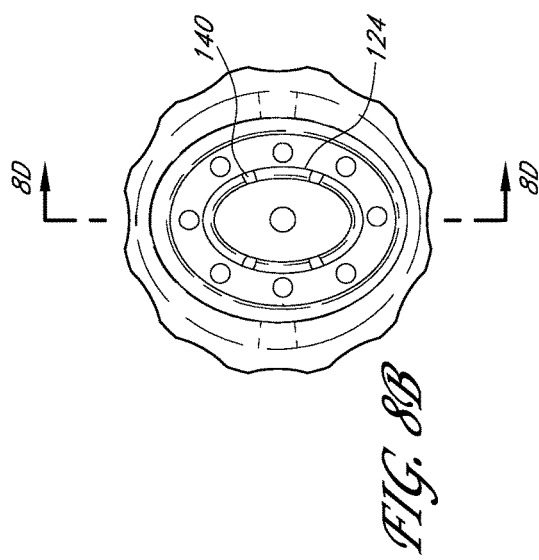
FIG. 8B is a top elevational view of the tip of FIG. 8A.
Figure 8D:
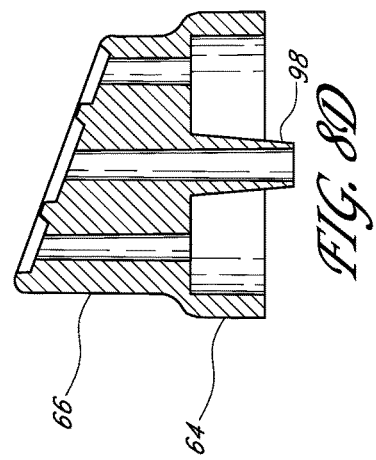
FIG. 8D is a cross-sectional view of the tip of FIG. 8B taken along the line 8D-8D.
Figure 8A:
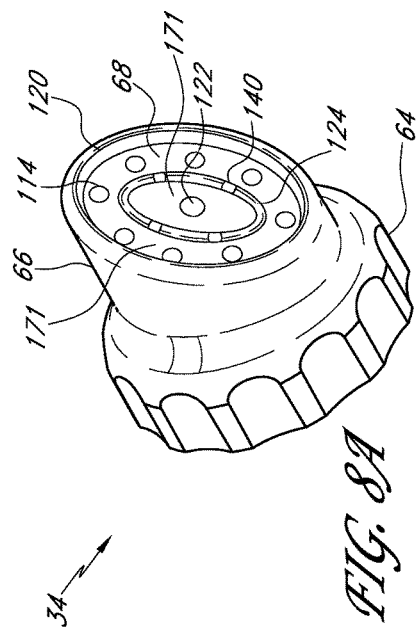
FIG. 8A is a perspective view of yet another embodiment of a tip for treating a person's skin.

The inner member 124 is preferably spaced from the outer member 120 to define one or more channels. The illustrated outer member 120 defines a continuous channel 140 that extends outwardly from the central through-hole 122 towards at least one of the outer through-holes 114. The inner member 120 can form the sidewalls of the channel 140. Any suitable configuration of channels 140 can be used to provide fluid flow along a flow path. The illustrated channels 140 have a somewhat U-shaped axial cross-sectional profile, as depicted in FIG. 8A. The channel 140 can have a V-shaped, curved, or any other suitable cross sectional profile. A flow path between the through-holes in the tip 34 can be defined at least in part by the channels.

The spiral-like pattern of the inner members 124 in FIGS. 5 through 7 varies. For example, the inner member 124 in FIG. 5 extends about a longitudinal axis 143 of the tip 34 approximately one and a half times, the inner member 124 in FIG. 6 extends about the tip 34 approximately two and a half times, and the inner member 124 in FIG. 7 rotates about the tip 34 approximately one and three quarters times. In some embodiments, the inner member 124 subtends an angle of about 70°, 135°, 180°, 210°, 225°, 270°, 315°, 360°, and angles encompassing such ranges. In yet other embodiments, the inner member 124 subtends an angle of about 405°, 450°, or 495°. The tightness of the spiral in combination with the location and number of through-holes 114 affects the detention time of the fluid in the channel 140. Generally, a tighter spiral results in a longer the pathway (i.e., the length of the channel 140) from delivery through-hole 122 to the return through-holes 114. Fluid traveling down the longer pathway is in contact with the person's skin 80 for a longer period of time. Thus, tighter spirals lead to increased contact time between the fluid and the skin 80. These longer contact times can increase the effectiveness of the fluid because the skin can absorb an adequate amount of active ingredients of the treatment material. Fluid retention time on the patient's skin can be increased to increase hydration, serum retention, and the like. Shorter pathways can be used to reduce contact time between the fluid and the patient's skin. In some embodiments, for example, the tip 34 of FIGS. 5A to 5D has a relatively short pathway to limit absorption of fluids, achieve relatively high flow rates, and the like.

Additionally, the inner members 124 can be configured to remove tissue. The inner member 124 can be an abrasive member designed to remove tissue when the inner member 124 slides along a person's skin. The user may select a tip 34 based on the appropriate detention time and abrasiveness for the treatment being applied. For example, the tip 34 illustrated in FIG. 7 will provide less abrasion than the tip illustrated in FIG. 6, but the tip 34 illustrated in FIG. 7 will provide a longer detention time than the tip 34 illustrated in FIG. 5.

The illustrated tip 34 includes a generally continuous inner member 124 that extends from near the through-hole 122 towards at least one of the through-holes 114. In other embodiments, the tip 34 can have a plurality of inner members 124. For example, the inner members 124 can be linear, curved, and may be continuous or discontinuous.

The handpiece assembly 18 can be moved while the spiral-like inner member 124 engages the patient's skin. The movement of the handpiece assembly 18 can increase the effectiveness of the treatment material expelled out of the tip 34. In some embodiments, for example, the tip 34 can be used with a lifting treatment material that facilitates extractions of, for example, sebum, blackheads, skin, or other substances (e.g., oils, dead skin, etc.). The lifting treatment extraction producer can unclog pores to improve the treated skin's overall appearance. To facilitate extractions, the handpiece assembly 18 can be twisted or rotated while the tip 34 is pressed against the patient's skin. The twisting action and the lifting treatment material can work in combination for effective extractions. In alternative embodiments, a handpiece assembly 18 can also be used without a lifting treatment material for extractions by employing the twisting motion.

In certain embodiments, the spiral-like tip 34 massages the skin 80. In other embodiments, the spiral-like tip 34 ablates the skin 80. For example, the inner members 124 may act as blades to cut thin layers from the skin 80 when the user twists the handpiece assembly 18. Twisting the handpiece assembly 18 causes the tip 34 to rotate about the twisting axis, rotating the sharp inner members 124 against the skin 80, which causes ablation. Thin layers of skin can thus be removed by the handpiece assembly 18. Additionally or alternatively, the spiral-like tip 34 may plane along skin when a fluid is applied to the skin. The planing tip 34 can remove a thin layer of the skin (e.g., the stratum corneum, preferably hydrated stratum corneum). Accordingly, the user can use the handpiece assembly 18 to remove a particular amount of skin.

A vacuum can be applied by the handpiece assembly 18. For example, the console 12 can have a pump that applies a vacuum via the output line 52. The negative pressure draws waste material into the through-holes 114 and out of the handpiece assembly 18. When the tip 34 engages the patient's skin, the vacuum can draw the skin against the tip 34 to enhance the effectiveness of the inner members 124. The vacuum can be increased or decreased to increase or decrease, respectively, for example, frictional forces, depth of cutting, amount of abrasion, and the like. To rapidly remove skin, a strong vacuum can be applied to the person's skin so that the skin is pulled against the inner member 124. The vacuum can also facilitated removal of the waste fluid captured between the tip 34 and the patient's skin. A vacuum can also be used in combination with the tips illustrated in FIGS. 1-10E. The vacuum can also be varied based on the thickness, compliance, and other properties of the skin surface The tip 34 can have any suitable number of through-holes 114, 122 to achieve the desired fluid flow between the skin 80 and the tip 34. For example, FIG. 5A to 5D illustrate an embodiment with two through-holes 114. The number of through-holes 114, 122 can be chosen based on the cross-sectional areas of the through-holes 114, 122 and the expected flow rate of the fluid through the channel 100. Preferably, one end of through-holes 114 is positioned between the inner member 124 and the outer member 120. In some embodiments, including the embodiments illustrated in FIGS. 5A through 7, the through-holes 114 are positioned generally midway between the outer member 120 and inner member 124.

The tips can also have one or more energy sources for delivering energy to the skin. Radiant energy, heat, and the like can be delivered to the skin by the tips. The tip 34 illustrated in FIGS. 6A to 6D has a pair of energy sources 151 in the form of LEDs. When the tip 34 is proximate the patient's skin, the LEDs 151 can deliver a desired amount of energy to the skin. The illustrated tip 34 has four LEDs; however, any number of LEDs can be employed.

In alternative embodiments, the tips can carry deployable material. The structure 151 can be in the form of a cavity or pocket that contain and carry material that is released when it engages the treatment fluid. The material in the cavities 151 can be made of any of the treatment materials disclosed herein, and can be in a solid form. For example, the cavities can hold lubricant or soap that is released when the tip is applied to skin.

Figure 8C:
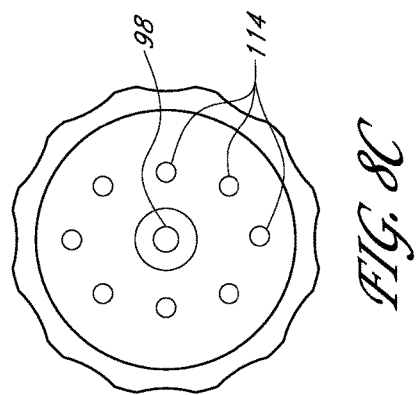
FIG. 8C is a bottom elevational view of the tip of FIG. 8A.

FIGS. 8A through 8D illustrate another embodiment of a tip 34 when the inner member 124 includes a ring with perforations 140 that provide fluid communication between the through-hole 122 and through-holes 114. A space 100 can be defined between the inner member 124, perforations 140, and outer member 120 when the tip 34 is in operative engagement with the skin 80. FIG. 8C illustrates an embodiment with eight through-holes 114. In the embodiment illustrated in FIGS. 8A through 8D, the inner member 124 forms recessed regions 171, allowing for a larger area of fluid contact with the skin 80 then the tips 34 illustrated in FIGS. 5 through 7.

FIGS. 9A through 9D illustrate another embodiment of a tip 34 comprising an outer member 120 and an array of protruding inner members 124. A recessed region 191 is defined between the inner members 124 and the outer member 120. The inner members 124 of FIGS. 9A to 9D can be posts that are similar to the inner members described above. The post 124, for example, can have relatively sharp edges. These edges can be used to remove skin. In some embodiments, the inner members 124 can have relatively sharp planing blades. The tip 34 illustrated in FIGS. 9A through 9D allows for more freedom of movement of the treatment fluid. The protruding inner members 124 preferably abrade the skin differently than the tips 34 illustrated in FIGS. 5A through 8. Rather than being able to ablate large sections of the skin 80 like a blade, as the tips 34 in FIGS. 5A-8 can do in certain embodiments, the plurality of protruding inner members 124 can ablate or roughen a plurality of smaller sections of the skin 80.

The protruding member 124 can optionally contain treatment material. For example, the protruding members 124 can be generally cylindrical members having a passageway or chamber 127 that holds treatment material. Thus, fluid can be used in combination with treatment material coupled to the tip 34.

With reference to FIGS. 5A through 9, the inner member 124 preferably has a height from the distal surface that is generally less than the height of the outer member 120. In some non-limiting embodiments, the height of the inner member 124 is less than 90%, 70%, 60%, 50%, and ranges encompassing such percentages of the height of the outer member 120. However, in other embodiments, the inner member 124 has a height that is generally greater than the height of the outer member 120. For example, the inner member 124 can have a height that is 10%, 20%, 30%, 40%, 50% greater than the height of the outer member 120. The inner member 124 can thus protrude from the tip 34. A skilled artisan can select a desired height of the inner member 124 and/or the outer member 120 to achieve the desired interaction with the person's skin 80.

FIGS. 10A through 10E illustrate another embodiment of a tip 34 comprising an outer member 120 and a pad 128. FIG. 10E depicts the pad 128 removed from the tip 34. The tip 34 preferably has a mounting surface 227 that is surrounded by the outer member 120. The pad 128 can be permanently or temporarily coupled to the mounting surface 227.

The pad 128 preferably has a distal surface 224 configured to treat a person's skin. In some embodiments, the pad 128 is a disposable pad that comprises treatment material attached thereto. For example, the pad 128 may comprise vitamins, moisturizers, antioxidants, and the like. Preferably, the pad 128 comprises an adhesive proximal side and a distal side 224 including an abrasive surface. The abrasive surface can have grit, a plurality of members (e.g., members similar to the inner members 124 described above), or the like. The pad 128 can be permanently coupled to the mating surface 227 so that the tip 34 can be used for an extended length of time, or for multiple treatments. In alternative embodiments, the tip 34 is removable for maximum flexibility in selecting pad abrasiveness, and also allows the user to make changes to the tip 34 without changing the tip 34 in its entirety. The grit rating of abrasive surface of the distal surface 224 can be selected based on the desired rate of skin removal.

The illustrated pad 128 is generally elliptical and planar. In alternative embodiments, the pad 128 can be polygonal, circular, or have any other shape as desired. The pad 128 can have cutouts 225 that can match the through-holes 114, 122. The cutouts 225 can be aligned with the through-holes 114, 122 when the pad 128 is coupled to the mounting surface 227 of the tip 34, as shown in FIGS. 10A to 10D. The illustrated mounting surface 227 defines a plurality of tip flow channels 229 extending between the through-holes 114, 122. When the tip 34 is assembled, fluid can flow along the channels 229 between the main body 66 and the pad 128.

Various types of adhesives can be used to temporarily or permanently couple the pad 128 to the mounting surface 227. As used herein, the term "adhesive" is a broad term and includes, but is not limited to, coupling agents, glues, bonding materials, or the like. In some embodiments, for example, waterproof pressure sensitive adhesives are used for releasably coupling the pad 128 to the mounting surface 227. In some embodiments, the pad 128 can be permanently coupled to the mounting surface 227. For example, the pad 128 can be bonded or fused to the main body 66. Additionally or alternatively, snap fittings, fasteners, or other coupling structures can be used to mount the pad 128.

The tip 34 described above can be used for wet or dry modes of operation. As such, the tip 34 can be used for wet exfoliation or dry exfoliation. In some embodiments, the tip 34 is used in a dry mode to remove a desired amount of skin. After removing a desired amount of skin, the tip 34 can be used in a wet mode on the same or different area of the patient's kin. During wet mode, fluid can be passed out of the tip 34 onto the patient's skin. The wet tip 34 can exfoliate, hydrate, and/or perform other types of treatments. Alternatively, the tip 34 can be used in a wet mode and than a dry mode. The sequence of wet and dry modes of operation can be selected based on the type of tip, treatment material, skin condition, and the like.

Although the handpiece assemblies are primarily discussed with respect to use with treatment material, the handpiece assemblies can be used without treatment material, i.e., the handpieces can be used in a dry procedure. Dry procedures can be used for non-hydration procedures and may require less post-procedure clean up.

Various fabrication techniques can be employed to make the tips 34 as mentioned above in connection with FIGS. 11A-11E. In some embodiments, the tips 34 are formed through a molding process, such as an injection or compression molding process. The tips 34 of FIGS. 5A to 5D, for example, can be monolithically formed through an injection molding process. Alternatively, the tip 34 of can have a multi-piece construction, if desired. The tips 34 can be made of polymers, rubbers, metals, or other suitable materials.

The tips 34 can also be fabricated in a multi-step process. For example, the main body 66 and skirt 64 can be formed in a single process. A textured surface (e.g., pad, inner members 124, etc.) can be applied to the main body 66 in a subsequent process. The textured surface can be formed by cutting, embossing, adding material (e.g., a pad, adhesive grit, etc.), a roughening implement, stamping process, or other suitable texturing means.

The tips can have associated treatment materials, including, for example, a medicament. As used herein, the term "medicament" is a broad term and includes, without limitation, growth agents, growth factors or hormones, growth inhibitors, serums, treatment material, cleaners, vitamins, exfoliators, lubricants, or other substances that can be used to treat a patient's skin. The medicament can be associated with the tip 34 by imbedding, overlaying, coating, impregnation, co-mixing, absorption, or other suitable means for associating the medicament with the tip 34. The medicament can be hardened so that it can further enhance massaging and/or abrasion. In some embodiments, the medicament forms hardened grit that can be imbedded on the surface of the tip 34. The grit can work in combination with the inner members 124 to treat a person's skin. If a fluid is used, the fluid can facilitate the release of the medicament from the tip 34. In some embodiments, the medicament comprises or more bioactive substances, such as antibiotics, substances for accelerating the healing of the wound, cell proliferation agents, and the like. Such bioactive substances may be desirable because they contribute to the healing of damaged or removed skin, as well as reducing the likelihood of infection.

FIGS. 11A to 11E illustrate different cross-sections of inner members that can be used with the tips illustrated in FIGS. 1-10E. The inner member 124 of FIG. 11A has generally sharp tip 253 for removing tissue. The tip 253 can have any suitable configuration for removing tissue from a patient. FIG. 11B illustrates an inner member 124 that has a pair of cutting edges 253 and a generally trapezoidal shape. FIG. 11C illustrates an inner member 124 that has a surface treatment 255 for treating a person's skin. The surface treatment 255 can be serrations, grooves, grit, roughed surface, protrusions, and the like. The type of surface treatment 255 can be selected based on the procedure to be performed. FIG. 11D illustrates another inner member 124 having a pair of cutting edges 253. The cutting edges 253 are spaced from each other and protrude outwardly. The central portion 257 is generally V-shaped; however, the central portion 257 can have other configurations. For example, FIG. 11E illustrates a central portion 257 that has a curved, semi-circular profile. In alternative embodiments, the inner member 124 can have more than two cutting edges.

The inner members 124 of FIGS. 11A to 11E can be formed by a molding process, such as an injection molding process. Additionally or alternatively, the inner members 124 can be formed by a machining process. For example, at least a portion of the inner member 124 of FIGS. 11D to 11E can be formed through a machining process. In some embodiments, the central portion 257 can be formed by cutting material out of the inner member 124. The fabrication process (e.g., molding, injection molding, compression molding, machining, milling, etc.) can be selected based on the design of the inner members.

Referring again to FIG. 1, the console 12 includes a manifold system 24 that holds containers 26 containing treatment fluids and/or antimicrobial agents. In a preferred embodiment, the console 12 holds four containers 26, three containing different treatment fluids and one containing an antimicrobial agent. In the illustrated embodiment, the largest container 26 holds antimicrobial agent for cleaning and sanitizing the fluid lines of the console 12. The containers 26 can also hold other suitable substances, such as surfactants, disinfectants, sanitizers, and the like, for cleaning and/or sanitizing the skin treatment system 10.

Figure 12:
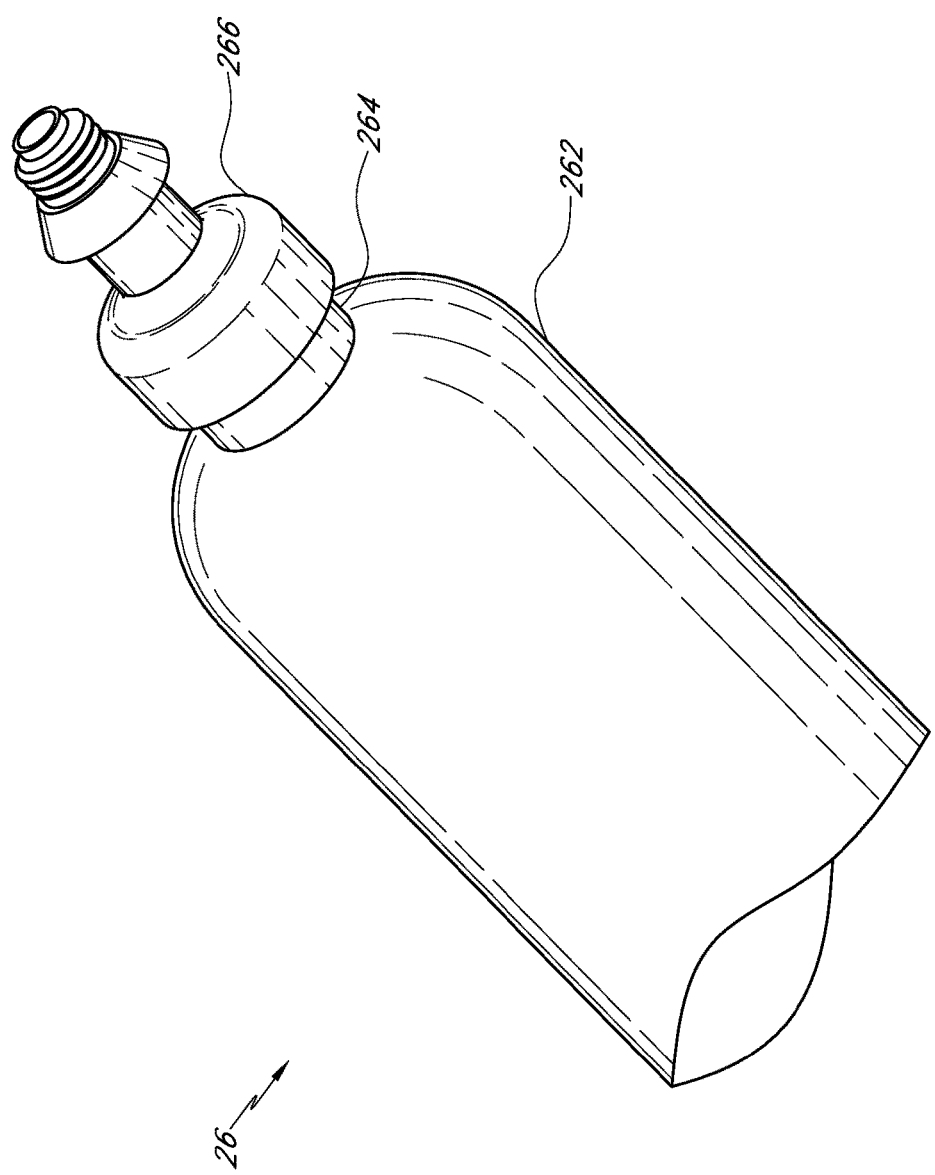
FIG. 12 is a perspective view of a bottle for use with the skin treatment system of FIG. 1.

As shown in FIGS. 12 and 12A, the container 26 can be a fluid source such as a bottle comprising a body 262, a neck 264, and a closure assembly 266. The neck 264 includes a threaded neck finish and the closure 266 includes a threaded interior surface, allowing it to screw onto the neck 264. The closure 266 can be permanently or temporarily coupled to the neck 264. The illustrated bottle 26 is a non-refillable, disposable bottle. As used herein, the term "non-refillable" is a broad term that includes, but is not limited to, components that cannot be easily refilled with a treatment material. For example, the illustrated non-refillable bottle 26 cannot be refilled without substantial difficulty.

Figure 13A:
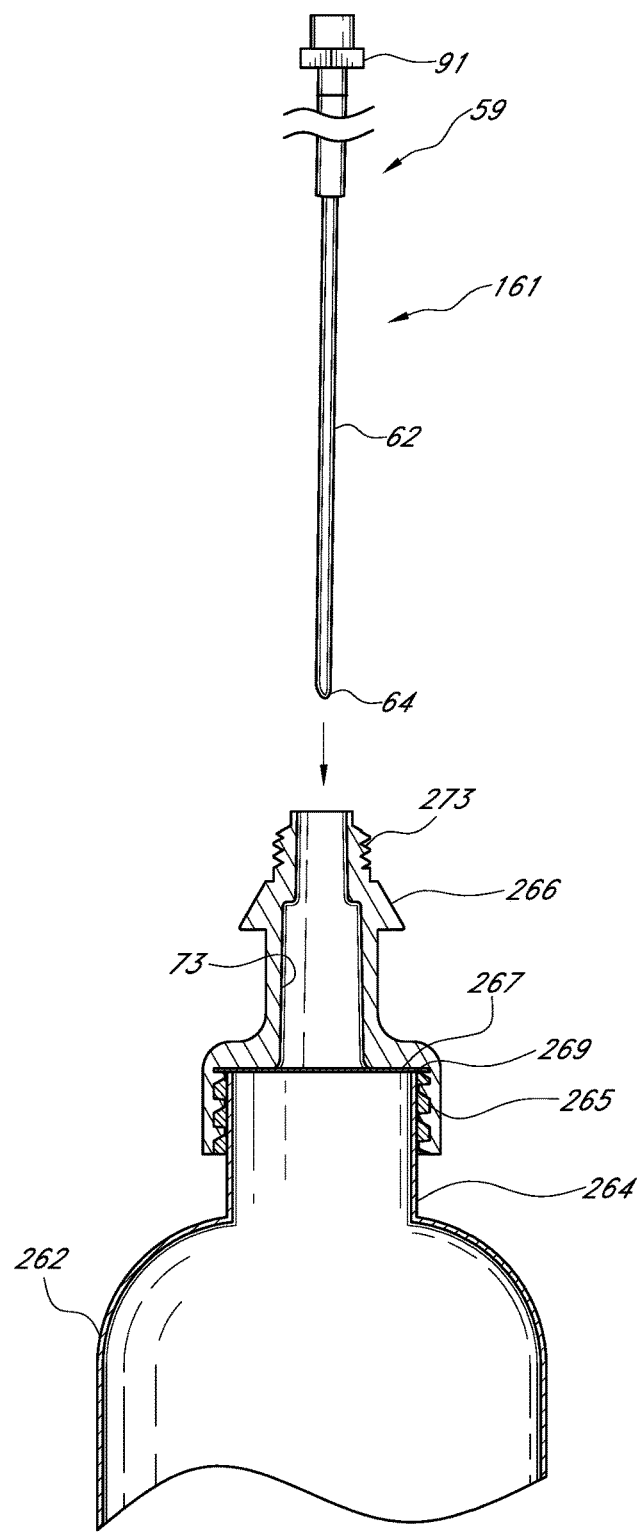
FIG. 13A is a cross-sectional view of one embodiment of a bottle spaced from an insertion tip assembly.

Bodies 262 of the containers 26 may be formed by stretch blow molding a preform into the desired shape. In other embodiments, the body 262 and a neck 264 can be formed by extrusion blow molding. For example, the bottle of FIG. 13A can be formed by extrusion blow molding. The containers 26 can be made of polymers, thermosets, thermoplastic materials such as polyesters (e.g., polyethylene terephthalate (PET)), polyolefins, including polypropylene and polyethylene, polycarbonate, polyamides including nylons, epoxies, and/or acrylics. The material can be virgin or post-consumer/recycled. However, other suitable materials known in the art can also be used.

In some embodiments, including the illustrated embodiment of FIGS. 12 and 12B, the closure 266 is welded (e.g., induction welded) to an upper edge 269 of the neck 264. A sealing member 267 can be interposed between the upper edge of the neck 269 and the closure 266. In some embodiments, the sealing member 267 is made out of a conductive metal, such as aluminum, that preferably does not react with the fluid in the bottle 26. In other embodiments, the seal 267 comprises plastic, such as cellophane, polypropylene, or other suitable material, preferably suitable for coupling to the closure 266 and upper edge 269. In some embodiments, the sealing member 267 comprises metal that is at least partially coated with a polymer, such as polypropylene. Induction welding can be used to couple the polypropylene to the closure 266 and neck 264, both of which can also comprise polypropylene.

Figure 13B:
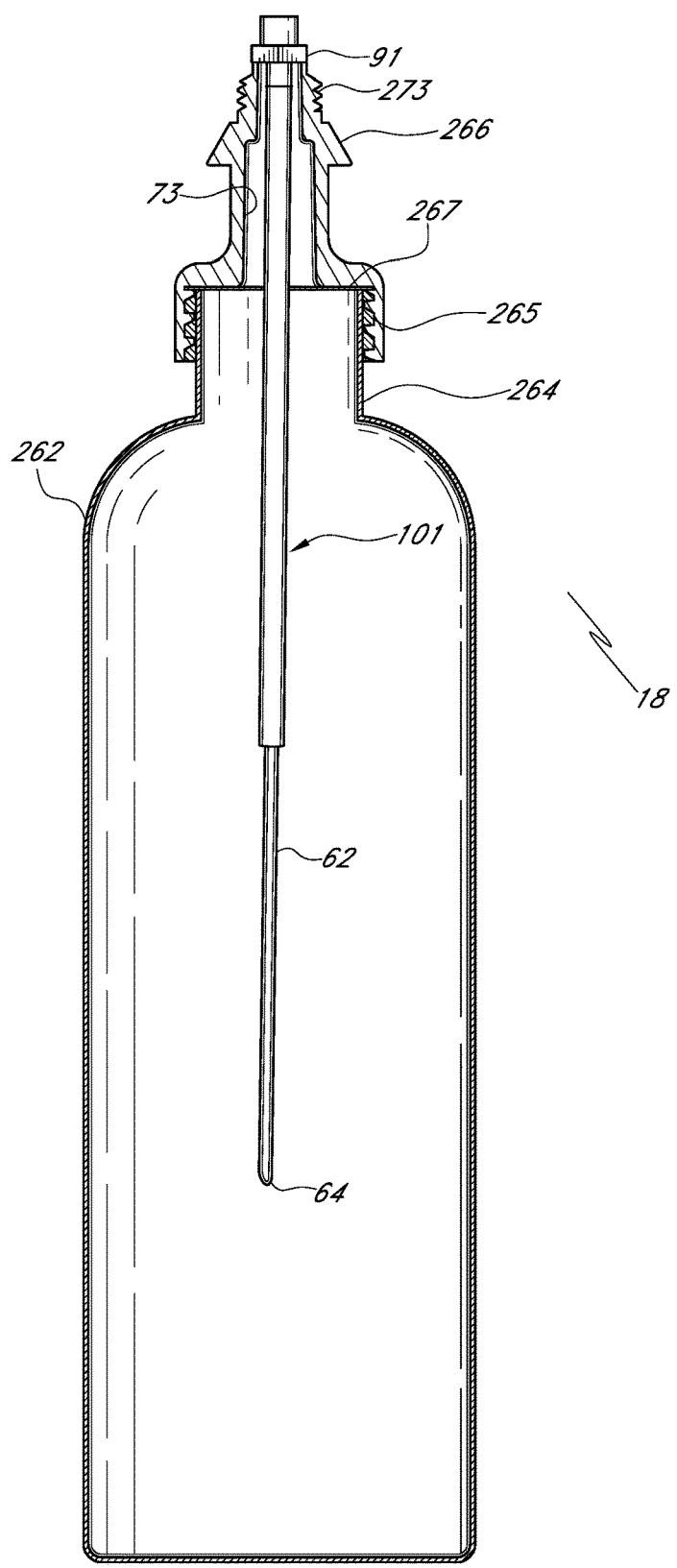
FIG. 13B is a cross-sectional view of the bottle of FIG. 12A coupled with the insertion tip assembly.
Figure 14A:
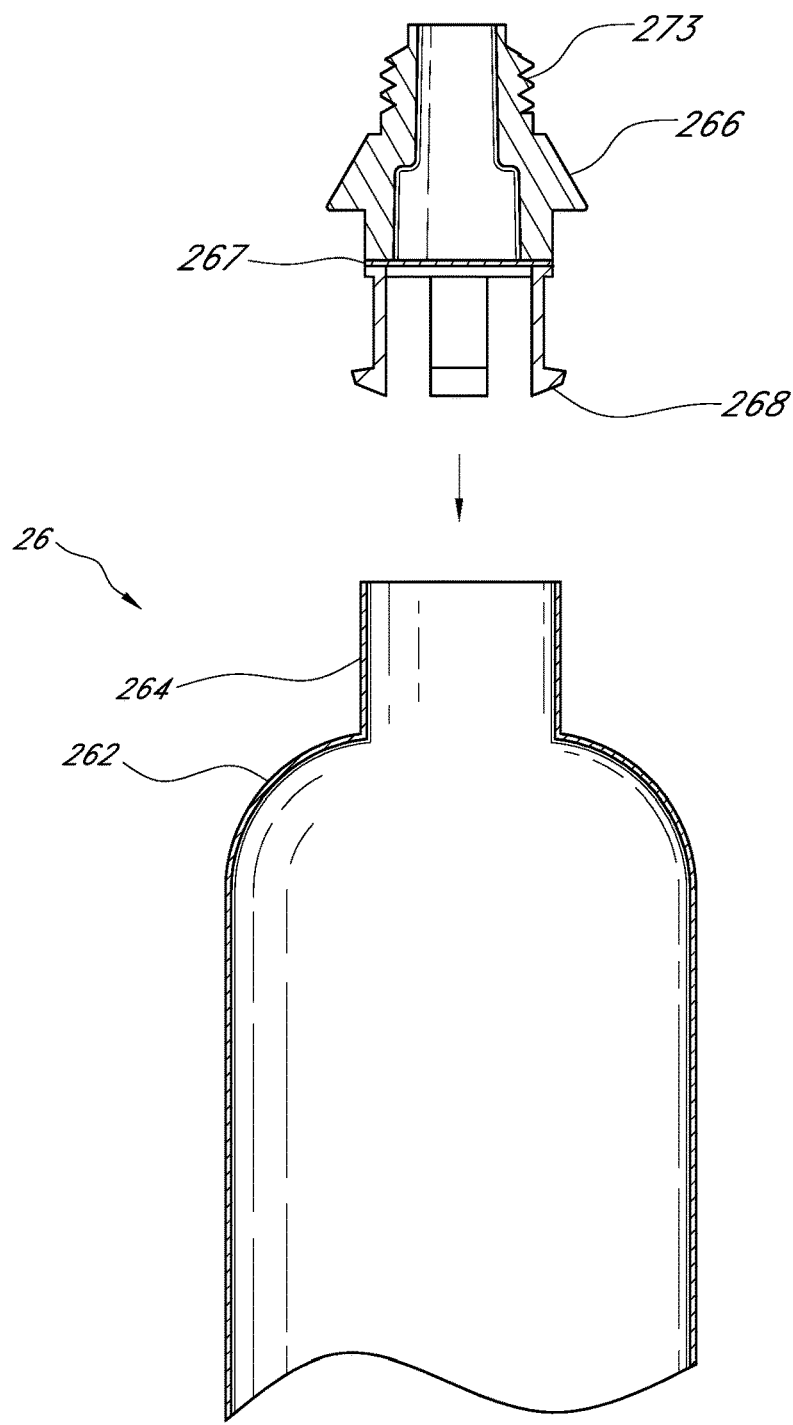
FIG. 14A is a cross-sectional view of a closure and a bottle.

FIG. 14A illustrates another embodiment of a bottle 26. The closure 266 includes locking members 268 that engage the neck 264, but do not allow removal of the closure 266 from the bottle 26 when assembled, as shown in FIG. 13B. The locking closure 266 may include a sealing member 267, for example as described above.

In either of the embodiments illustrated in FIGS. 12 through 14B, the closure 266 may then be sealed with a second closure (not shown), creating multi-piece closures. For example, a screw cap can be threaded onto the external threads 273 at the top end of the closure 266. In these embodiments, the treatment fluid inside the bottle 26 may be accessed by puncturing or otherwise breaking the seal 267, for example with an insertion tip assembly 59 (see FIG. 13A).

The insertion tip assembly 59 has an elongate member 161 that comprises a fluid pick up conduit 62 and lancing tip 64 extending from the distal end of the conduit 62. In the illustrated embodiment, the lancing tip 64 is a tubular member having a somewhat sharp distal end. To access treatment fluid in the bottle 26, the lancing tip 64 can be inserted into the closure passageway 73 of the closure 266. The lancing tip 64 can be advanced through the passageway 73 until it breaks the sealing member 267. The elongate member 161 can be sufficiently rigid such that it can break the sealing member 267 without buckling. The elongate member 161 can comprise metal, polymers, plastics, or any suitable material.

The fluid pick up conduit 62 and lancing tip 64 can be slid through the passageway 73 until the stop 91 is spaced from the upper edge of the closure 266. In alternative embodiments, the insertion tip assembly 59 can be slid through the passageway 73 until the stop 91 contacts the upper edge of the closure 266, as shown in FIG. 12B. After the insertion tip assembly 59 and bottle 26 are assembled, as shown in FIG. 12B, the treatment material can be draw upwardly through the lancing tip 64 and the fluid pick up conduit 62. The treatment material can flow through a passageway of the insertion tip assembly 59 and to the manifold assembly 24.

In certain embodiments, the treatment fluid applied from the containers 26 may be selected from the console 12 for a particular treatment or skin type. In one embodiment, the treatment fluid may comprise a skin rejuvenation serum. Skin rejuvenation serum cleans the skin 80 deeply while softening sebum and impurities to aid in extractions. Skin rejuvenation serum also assists in dislodging dead cells for extraction and exfoliation by the tip 34 as well as providing residual hydration that aids in firming and smoothing fine lines, resulting in clean, refined, and ultra-moisturized skin 80. Preferably, a skin rejuvenation treatment serum is active-4™, available from Edge Systems Corp., 2277 Redondo Ave., Signal Hill, CA, 90755, (800) 603-4996. In another embodiment, the treatment fluid may comprise a salicylic acid serum. A salicylic acid serum cleans oily skin deeply while softening sebum and impurities to aid in extraction and exfoliation by the tip 34. Hydration additives in the salicylic acid serum create an ultra-moisturized skin surface, and is blended to remain on the face for the best possible benefit. Preferably, a salicylic acid treatment fluid is Beta-hd™, also available from Edge Systems Corp. In yet another embodiment, the treatment fluid may comprise antioxidants. The antioxidant serum is a hybrid that combats free radicals and environmental damage to the cells. The antioxidant serum is formulated with a blend of the most effective antioxidant ingredients. The antioxidant serum is an absorbable, leave-on service that improves the appearance of age signs as well as texture and clarity. Preferably, an antioxidant treatment fluid is antiox-6™, also available from Edge Systems Corp. The treatment fluids may comprise agents known to be beneficial to skin healing and/or hydration including but not limited to glucosamine, laminaria digitata extract, yeast extract, carbamide, lactic acid, sodium lactate, honey extract, pentylene glycol, spirea ulmaria extract, camellia sinensis leaf (white tea) extract, horse chestnut extract, stabilized vitamins A, B1, B6, B12, C, and E, tocopherol, inositol, calcium panthothenate, linoleic acid, *rosemarinus officinalis* extract, biotin, and aloins such as anthraquinone gycosides, polysaccharides, sterols, gelonins, and chromones.

A single treatment may comprise the serial use of several treatment fluids from the containers 26. For example, the treatment of acne prone skin may comprise salicylic treatment followed by antioxidant treatment, the treatment of aging skin may comprise skin rejuvenator treatment followed by salicylic treatment followed by antioxidant treatment, the treatment of congestion (e.g., blackheads) may comprise skin rejuvenator treatment followed by salicylic treatment followed by antioxidant treatment, the treatment of damaged skin (e.g., due to medication or smoking) may comprise skin rejuvenator treatment followed by antioxidant treatment, the treatment of skin may comprise skin rejuvenator treatment followed by salicylic treatment followed by antioxidant treatment, the treatment of hyperpigmentation may comprise skin rejuvenator treatment followed by salicylic treatment followed by antioxidant treatment, the treatment of melasma may comprise skin rejuvenator treatment followed by salicylic treatment followed by antioxidant treatment, the treatment of sensitive skin may comprise skin rejuvenator treatment followed by antioxidant treatment, and the treatment of thin skin may comprise salicylic treatment followed by antioxidant treatment. Alternatively, a single treatment may comprise the parallel use of a combination of treatment fluids from the containers 26, for example using a handpiece with a plurality of input lumens 90 as described above. Treatment time with each treatment fluid is preferably about 2 to 20 minutes, but may be longer or shorter depending on the patient, the tip 34 used, and the treatment itself.

The treatment materials can be used for acne (e.g., by removing oils, bacteria, etc.), melasma, damaged skin (e.g., sun damaged skin, burns, free radical damage, etc.), extractions, skin lightening and/or brightening, skin lines (e.g., fine lines, wrinkles, creases, etc.), dry skin, and the like. The treatment materials can improve skin elasticity and overall health of the skin. For example, if the skin is damaged, antioxidants can be applied to damaged area. Accordingly, the skin treatment system 10 can be used to improve the health, appearance, and/or function of a person's skin.

Additionally, the line 20 may be periodically flushed with a fluid (e.g., a antimicrobial fluid, water, etc.) contained in one of the containers 26. Antimicrobial fluids can contain any disinfecting agent compatible with skin including, but not limited to, butylene glycol, phenoxyethanol, and methyl isothiazolinone. Preferably, an antimicrobial fluid is Rinseaway™, Available from Edge Systems Corp. The Line 20 should be Flushed with antimicrobial fluid at least at the end of each service day. Flushing with antimicrobial fluid is more important when the system is not used for consecutive days.

As illustrated in FIG. 1, the console 12 comprises the manifold system 24 designed to draw treatment fluid from at least one of the containers 26 based on user selection. The manifold system 24 may include switches 29, each corresponding to one of the bottles. The switches 29 can be used to control fluid flow from the containers 26. The illustrated switches 29 can be used to turn Off/On to permit or prevent fluid flow from the bottles 26. The illustrated manifold system 24 has a switch corresponding to each bottle 26. As such, the switches can be used to independently control fluid flow from each of the bottles 26. In other embodiments, a single switch can be used to control the flow of treatment fluid from more than one of the bottles 26.

Figure 14B:
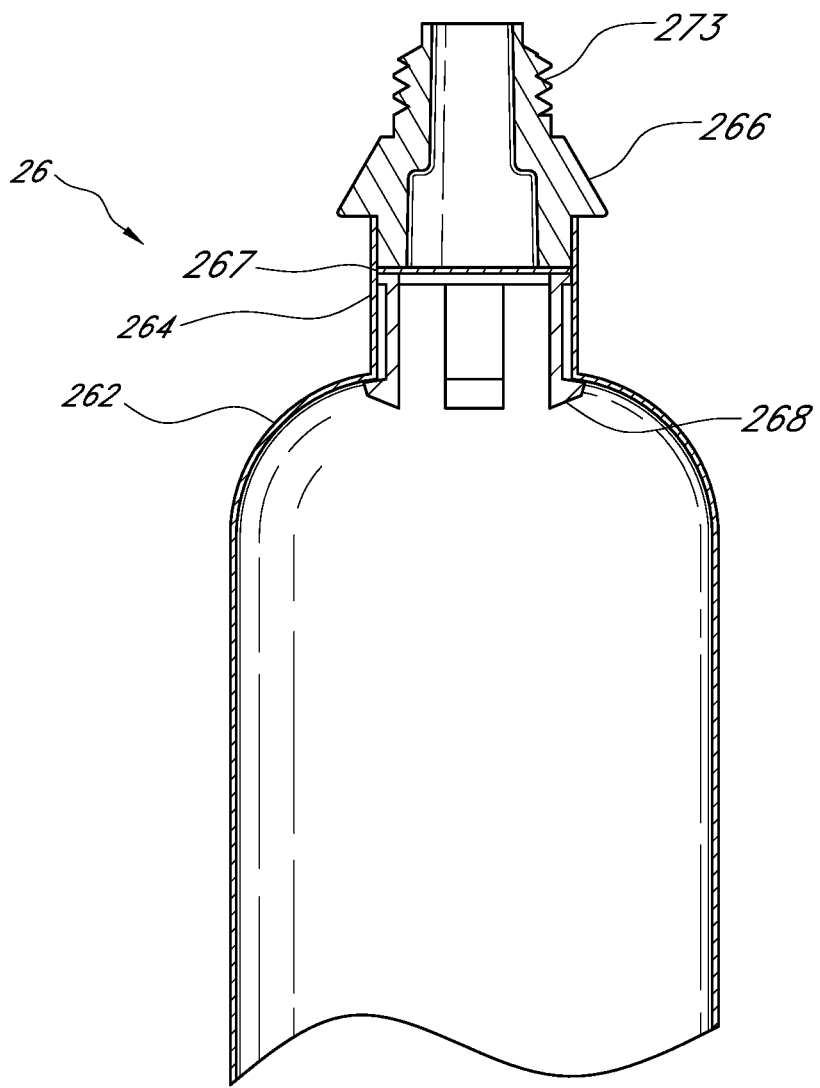
FIG. 14B is a cross-sectional view of the closure and bottle of FIG. 14A when assembled.

With continued reference to FIG. 1, the button 246 can be operated to release a corresponding bottle 26 from the manifold system 24. FIG. 15A is front perspective view an embodiment in which the manifold system 24 contains quick-release locks connected to the button 246, wherein the quick-release locks capture the containers 26. As illustrated in FIGS. 14B and 14C, the quick-release locks 242 engage the closure 266 when the bottle 26 is inserted into the manifold system 24. When the quick-release lock 242 is manually engaged by a user, for example by pulling the button 246, a slide structure 249 surrounding the closure 266 releases, thereby releasing the bottle 26 from the manifold system 24.

Figure 15C:
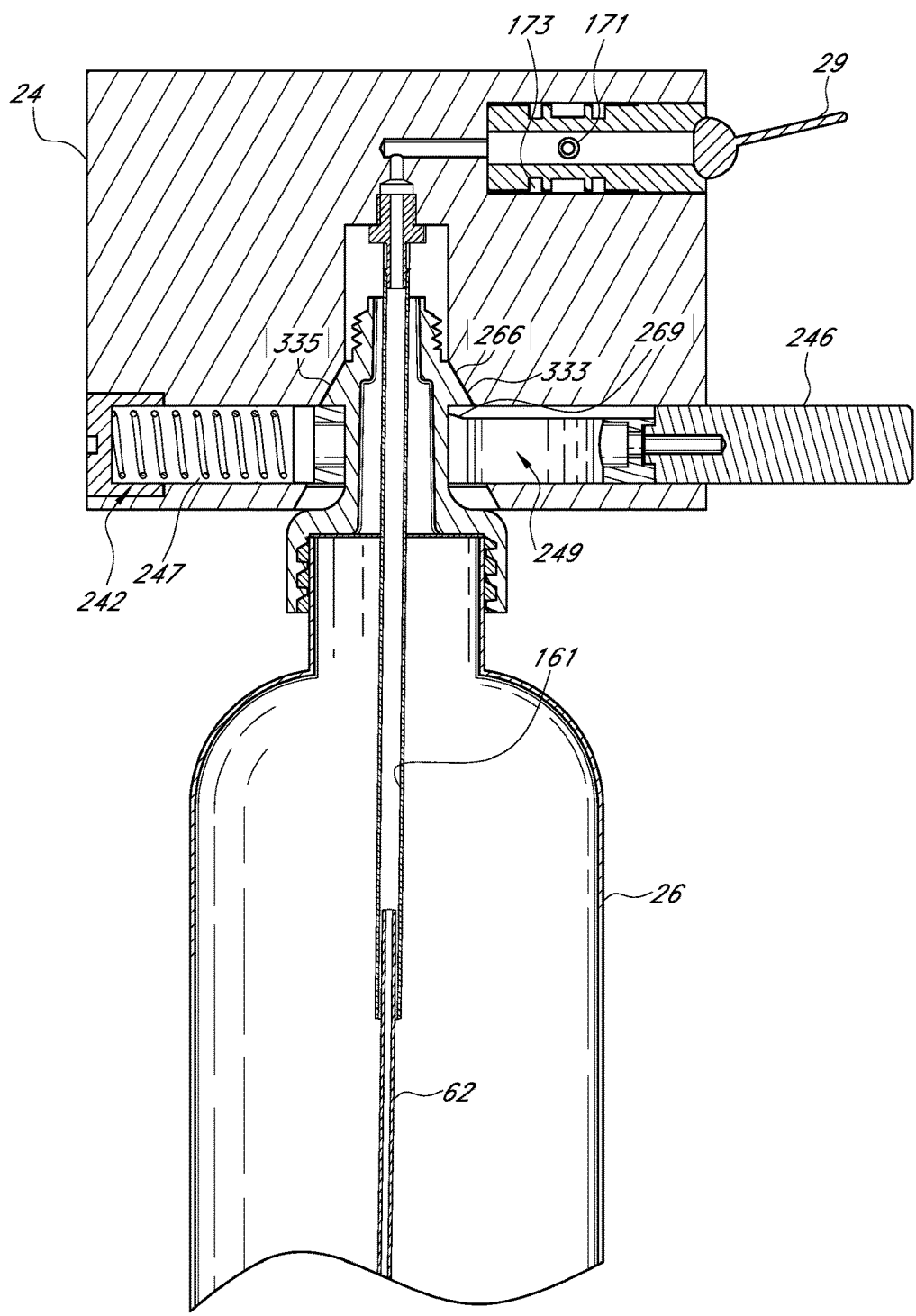
FIG. 15C is a cross-sectional view of the manifold system of FIG. 15A taken along the line 15C-15C of FIG. 15A.
Figure 15D:
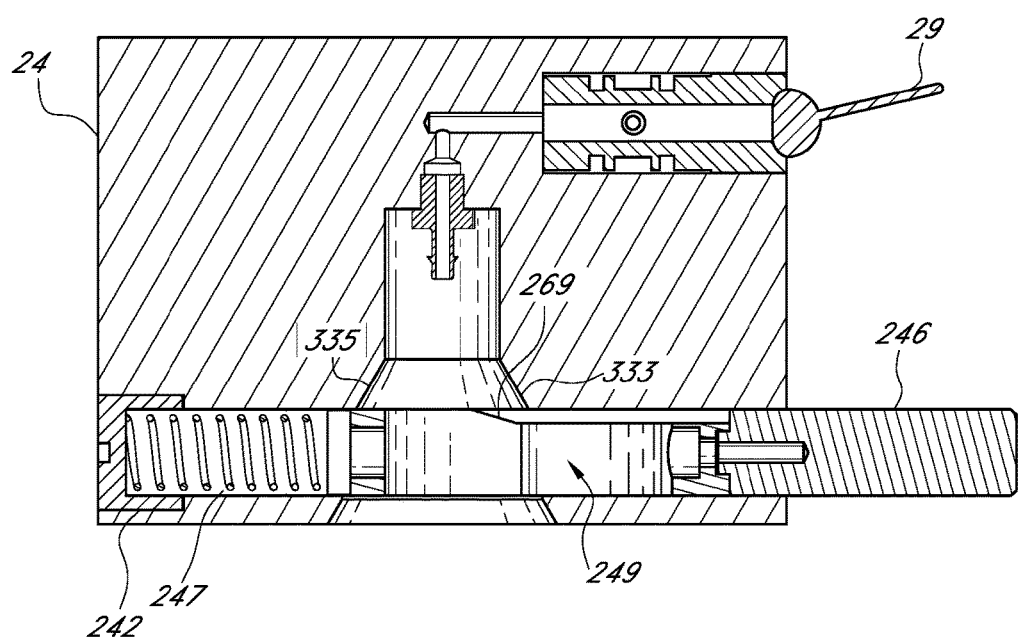
FIG. 15D is a cross-sectional view of the manifold system of FIG. 15C wherein the bottle has been removed.
Figure 15E:
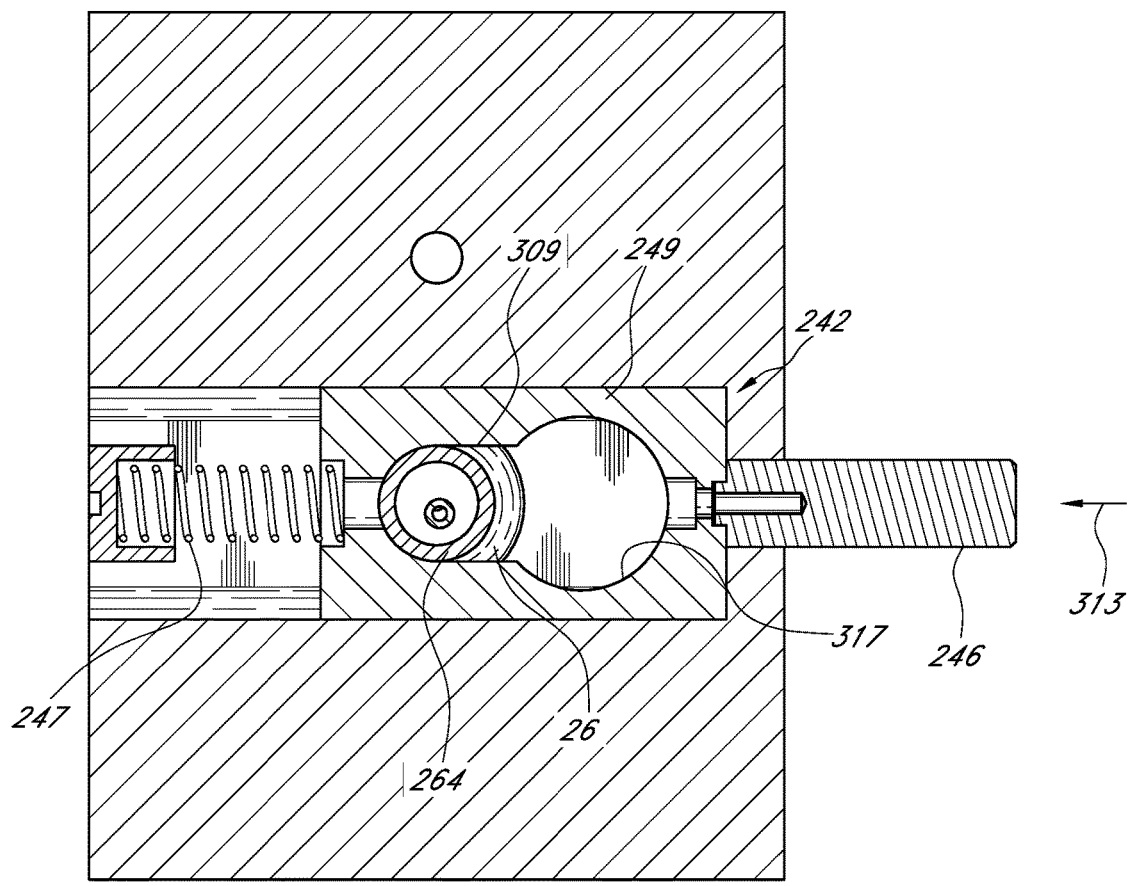
FIG. 15E is a cross-sectional elevational view of the manifold system.

FIG. 15E illustrates the slide structure 249 holding the neck 264 of the bottle 26 in an elongated slot 309. The button 246 can be pushed inwardly (indicated by the arrow 313) so that the neck 264 is positioned within the enlarged aperture 317. The bottle 26 can then slide downwardly out of the manifold system 24. The bottle 26 can be replaced with another bottle 26.

To couple the bottle 26 to the manifold system 24, the closure 266 can be inserted through the aperture 317 of the slide structure 249 when the button 246 is pushed in. Once the closure 266 engages the stop surface 333 (FIG. 15C), the spring 247 can push the slide structure 249 until the flange 335 of the bottle 26 rests on the slide structure 249, as shown in FIG. 15C. In such a position, the manifold system 24 securely holds the bottle 26. The illustrated slide structure 249 has a sloped portion 269 that can cam along the flange 335 as the button 246 moves outwardly. Accordingly, the slide member 249 can push the closure 266 upwardly until the closure 266 is locked with the manifold 24, as shown in FIG. 15C. The quick-release lock 242 is loaded with spring 247 such that the slide structure 249 is biased towards the button 246.

The manifold system 24 can have a modular design so that it can be removed from the console 12. In some embodiments, the manifold system 24 and associated containers 26 can be removed and transported away from the console 12. Accordingly, the modular manifold systems can be interchanged to provide treatment flexibility. Alternatively, the manifold system 24 can be permanently mounted to the console 12.

FIGS. 15B and 15C illustrate cross-sectional views of the manifold system 24 taken along lines 15B-15B and lines 15C-15C, respectively. Both FIGS. 15B and 15C show the fluid pick up conduit 62 in operative engagement with the bottle 26 through the seal 267. Suction device(s) is preferably in fluid communication with the fluid pick up conduit 62, and draws fluid out of the bottle 26 through the fluid pick up conduit 62. The fluid can flow through a passageway 161 (see FIG. 15C) extending through the pick up conduit 62. The fluid can flow to and through the lumen 171 towards the line 20. If the switch 29 is off, the fluid from one or more of the upstream bottles can flow along the passage 173. The manifold system 24 then directs the fluid into the line 20.

In certain embodiments, including the embodiment of FIG. 1, the console 12 comprises a computer with display 32. In one embodiment, the display 32 is a user input device comprising a touch screen that controls the computer. In other embodiments, the computer may be controlled by input devices such as a keyboard, keypad, mouse, pointing device, or other input device. The computer controls a variety of functions in the console 12. For example, the computer may control the manifold system 24, and thereby the flow of treatment fluids from the containers 26. In one embodiment, the fluid flowing through the line 20 can be changed by pressing a single button on the touch screen display 32. In another embodiment, the computer contains teaching tutorials that are exhibited on the display 32. In yet another embodiment, the user may change program chips within the computer according to treatment and/or patient. In still another embodiment, the computer records patient and treatment data, for example data gathered during treatment.

The console 12 can also comprise a mechanical system for controlling fluid flow from the containers to the handpiece. One or more pumps, valves, fluid lines, and the like can cooperate to deliver fluid from the containers to the handpiece. The console 12 can be powered pneumatically, electrically, or by any other suitable powering means. The mechanically drive console 12 can have manual controls for controlling fluid flow to the handpiece.

The console 12 can also comprise additional handpieces suitable for other types of skin treatment. These additional handpieces can be used for pre-treatment or post-treatment in combination with other modalities. For example, the console 12 may include a handpiece for diamond tip abrasion, or "crystal-free" microdermabrasion, as described above. Such a handpiece may be useful for more aggressive treatments, in addition to treatment with the handpiece assembly 18. The diamond tips can range from fine to extra coarse.

In some embodiments, the console 12 comprises a handpiece including at least one light emitting diode (LED). Light therapy has been shown to improve skin. For example, red light between about 600 and about 700 nanometers and infrared LED light between about 700 and about 1,000 nanometers reduces the appearance of fine lines and superficial hyperpigmentation. For another example, blue LED light at about 430 nanometers improves the appearance of oily and acne-prone skin. Other benefits of light therapy include promotion of collagen production, increased circulation and moisture retention, smoothing of skin texture, and improvement of skin firmness and resilience.

The console 12 can comprise handpieces for vacuum therapy such as lymphatic drainage and cellulite massage. Vacuum therapy enhances the effects of treatment with the handpiece assembly 18 and LED light therapy. Preferably, the vacuum therapy handpieces are sized appropriately for facial massage and body massage. An example of a multi-modality protocol using a plurality of handpieces comprises diamond tip abrasion, treatment with handpiece assembly 18 and at least one treatment fluid from containers 26, vacuum therapy, red light therapy, and application of sunscreen, for example at a minimum skin protection factor (SPF) of 15. The various modalities may be included and ordered by the user depending on the desired outcome of the overall treatment.

The console 12 optionally includes any of a plurality of additional features. For example, a digital camera may be used to take pictures of the patient before and after treatment, and the pictures may be stored on the computer. The computer may hold client medical and treatment records. The computer may be connected to a network. The console 12 may store disks. The console 12 may include an ultrasound unit. The console 12 may include a stimulator, such as an electrical stimulator. The console 12 may include an iontophoresis handpiece. The number of additional features is limitless when considering the range of features that a user may wish to incorporate with the treatment provided by the handpiece assembly 18.

Figure 16:
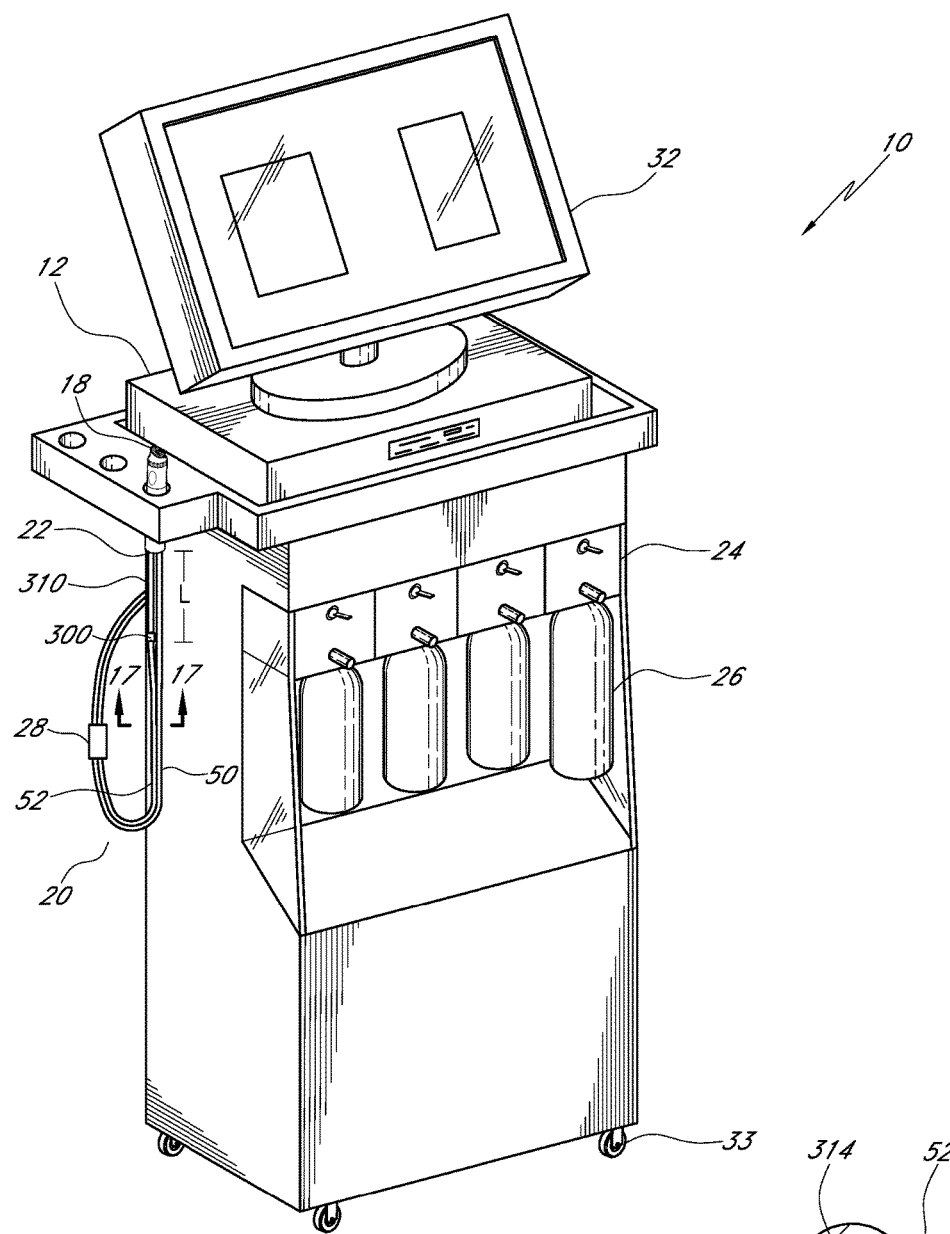
FIG. 16 is a perspective view of another embodiment of a skin treatment system.

FIG. 16 depicts another embodiment of the skin treatment system 10, which may be generally similar to the embodiment illustrated in FIG. 1, except as further detailed below. Where possible, similar elements are identified with identical reference numerals in the depiction of the embodiment of FIG. 1.

The line 20 includes an output line 50 for removing waste from the handpiece assembly 18 and an input line 52 for delivering treatment material to the handpiece assembly 18. A valve 300 can be disposed along the input line 52 to inhibit backflow of treatment material. The console 12 can pump treatment material through the input line 52 to the handpiece assembly 18 when the handpiece assembly 18 is applied to the person's skin, as detailed above. The fluid flow through the input line 52 can be reduced or stopped so that the handpiece assembly 18 can be removed from the patient's skin. The valve 300 can inhibit the flow of fluid through the input line 52 towards the console 12. A desired amount of treatment material can therefore be contained in the handpiece assembly 18 and the section 310 of the input tubing 52 extending between the valve 300 and the handpiece assembly 18. When the handpiece assembly 18 is applied to a patient's skin, a vacuum can be applied to the output line 50. The vacuum can draw the treatment material out of the handpiece assembly 18 without a substantial or noticeable delay.

In some embodiments, the valve 300 can be a one-way valve, such as a duckbill valve, check valve, or other type of valve for inhibiting fluid flow. In alternative embodiments, the valve 300 can comprises a plurality of valves (e.g., one-way valves, flow regulators, adjustable valves, etc.).

Figure 17:
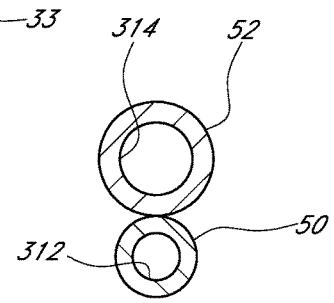
FIG. 17 is a cross-sectional view of a fluid line of the skin treatment system of FIG. 16 taken along the line 17-17.

FIG. 17 is a cross-sectional view of the line 20. The input and output lines 50, 52 can have different or similar cross sectional flow areas. The illustrated output line 50 has a passageway 312 with a diameter that that is less than the diameter of a passageway 314 of the input line 52. Accordingly, a relatively large slug of treatment material can be stored in the section 310 extending distally from the valve 300 to the handpiece assembly 18. The slug can be quickly delivered out of the handpiece assembly 18 once the handpiece assembly is applied to a patient's skin as detailed above.

In some embodiments, the section 310 of the output line 50 has a length L greater than 6 inches, 12 inches, 18 inches, 24 inches, and ranges encompassing such lengths. In some embodiments, the section 310 of the output line 50 has a length L greater than 24 inches, 30 inches, 36 inches, and ranges encompassing such lengths. The passageway 312 can have a cross-sectional area that is at least 10%, 30%, 50%, 75%, or 100% greater than the cross-sectional area of the passageway 314. The length L and the diameters of the passageways 312, 314 can be selected based on the desired amount of treatment material to be stored in the line 20, delivery and removal rates.

Figure 18:
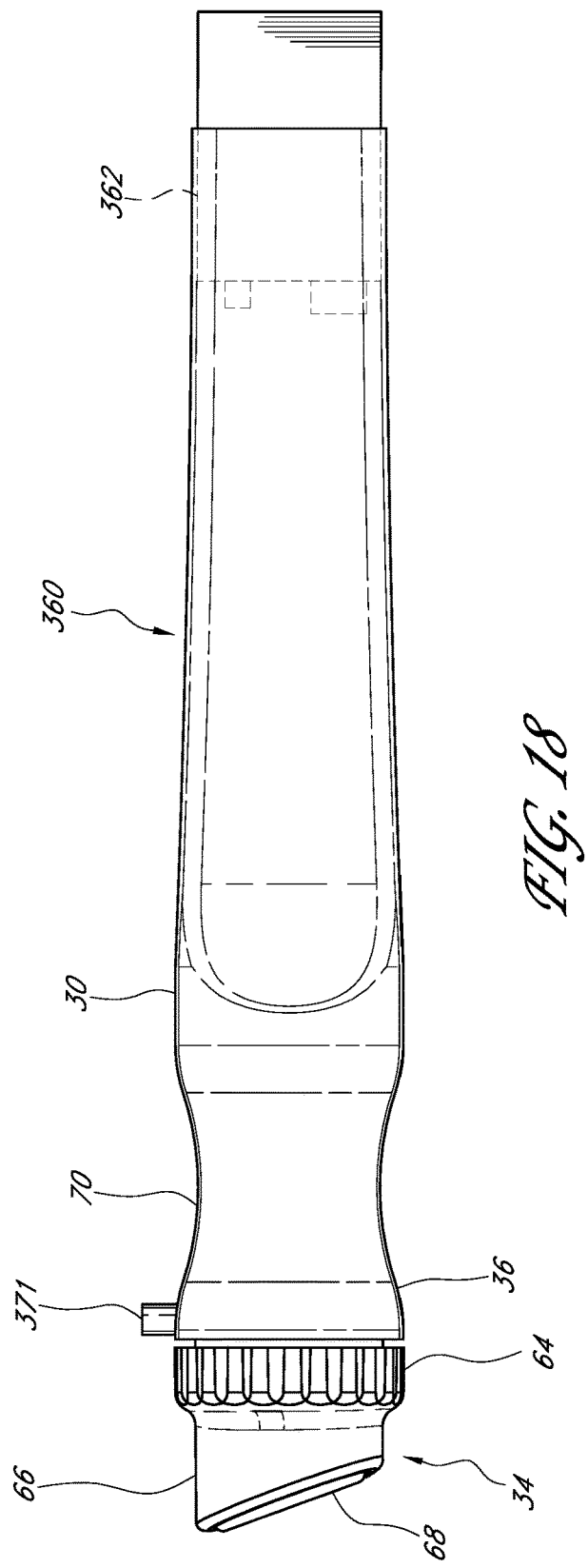
FIG. 18 is a side elevational view of a handpiece assembly with a removable cartridge.
Figure 19:
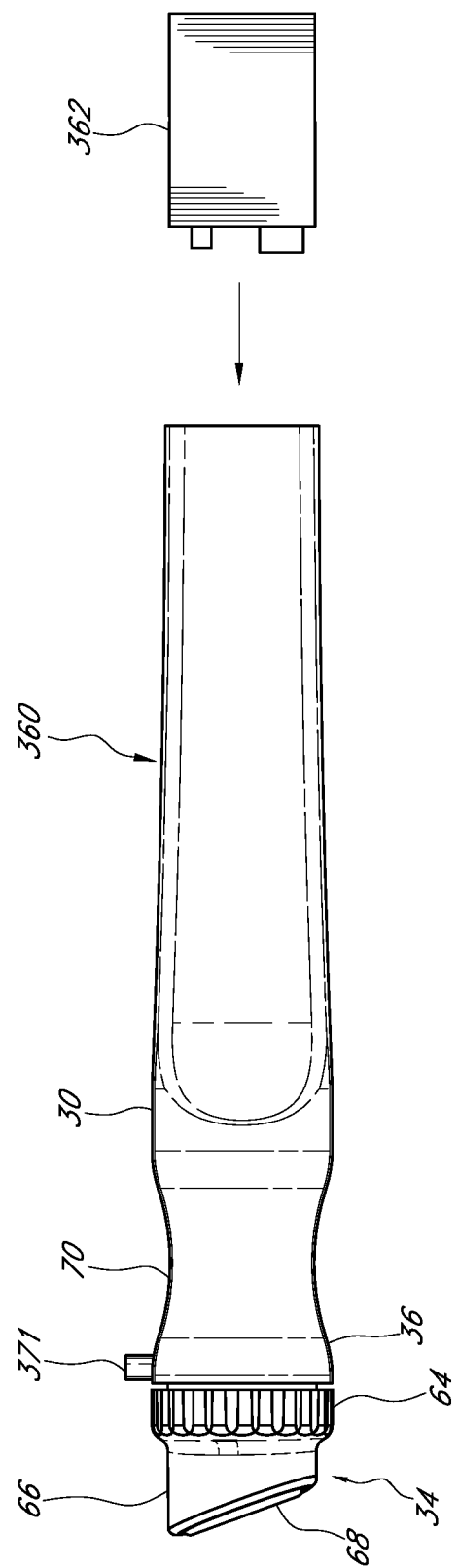
FIG. 19 is a side elevational view of the handpiece assembly and removable cartridge of FIG. 18, the cartridge is shown removed from the handpiece assembly.

FIGS. 18 and 19 illustrate a modular handpiece assembly 360 having a cartridge 362 containing treatment material. The illustrated handpiece assembly 360 can be used to deliver treatment material from the cartridge 362. The main body 30 can have a pump for pressuring the treatment material. In one embodiment, the fluid control device includes a power supply, such as a battery, which provides power to electrical components (e.g., pumps or valves) of the handpiece assembly 360. The power supply can be a battery that is preferably disposed within the main body 30 of the handpiece assembly 360. In one arrangement, the battery is a rechargeable battery that can be connected to and recharged by an AC power supply, such as a typical residential electrical outlet. Alternatively, the handpiece assembly 360 can be directly powered by an AC power supply. The power supply can provide power to several components of the handpiece assembly 360. For example, the power supply can provide power to a plurality of fluid control devices 330 and/or a flow control unit. A control switch 371 can be used to turn the handpiece assembly 360 Off/On and/or control the output of the handpiece assembly 360.

In operation, the cartridge 362 can be inserted into the main body 30. The handpiece assembly 360 can be applied to a patient's skin to deliver treatment material from the cartridge 362 to the patient's skin. After delivering a desired amount of treatment material, the cartridge 362 can be separated from the main body 30. The cartridge 362 can be a one-use or multi-use cartridge. For example, the cartridge can be a non-refillable disposable cartridge.

The tip 34 can also be used to remove hair or perform other skin treatments. For example, the tip 34 can include one or more razor blades and may be configured to apply a treatment material (e.g., antioxidants, vitamins, serums, growth agents, etc.) to the skin during the shaving process. In such embodiments, the main body 30 can be an elongated handle that is connected to a transversely extending elongate tip 34. In some embodiments, the handpiece assembly can be in the form of a disposable handheld razor. The treatment material can reduce or substantially eliminate problems associated with wet or dry shaving systems. These treatment materials may be applied prior to, during, before, and/or after shaving.

The articles disclosed herein may be formed through any suitable means. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

What is claimed is:

1. A tip configured for use in a skin treatment system, comprising:
    a tip body extending from a proximal end to a distal end of the tip, the proximal end being configured to couple to a handpiece assembly;
    at least one first passage extending through an interior of the tip body and configured to receive a fluid and to deliver said fluid to the distal end of the tip;
    at least one second passage extending through an interior of the tip body and configured to convey fluid and debris away from the distal end of the tip;
    an outer member defining a periphery along the distal end, the outer member being configured to contact skin during a treatment procedure; and
    at least one inner member located within an inner area of the outer member, wherein the at least one inner member comprises a spiral-like pattern;
    wherein the at least one inner member is configured to abrade skin.

2. The tip of claim 1, wherein the at least one inner member extends about the tip 1.5 or 2.5 times.

3. The tip of claim 1, wherein the at least one inner member extends from near a center portion of the inner area at a first end to near a lateral edge of the inner area at a second end.

4. The tip of claim 1, wherein the at least one inner member extends continuously from a first end to a second end of the at least one inner member.

5. The tip of claim 1, wherein the tip further comprises an imbedded treatment material.

6. The tip of claim 1, wherein the tip is configured to removably couple to the handpiece assembly.

7. The tip of claim 1, wherein the tip is disposable.

8. The tip of claim 1, wherein the tip is monolithically formed.

9. The tip of claim 1, wherein a radius of the at least one inner member relative to a central point of the tip varies at least a portion of a length of the at least one inner member.

10. A tip configured for use in a skin treatment system, comprising:
    a tip body extending to a proximal end of the tip, the proximal end of the tip being configured to couple to a handpiece assembly;
    at least one vacuum hole configured to receive fluid and debris transferred away from a distal end of the tip body;
    an outer member defining a periphery along the distal end; and
    at least one inner member located within an interior area of the outer member, wherein the at least one inner member comprises a spiral-like pattern;
    wherein the at least one inner member is configured to abrade skin.

11. The tip of claim 10, wherein the tip further comprises an imbedded treatment material.

12. The tip of claim 10, wherein the tip is configured to removably couple to the handpiece assembly.

13. The tip of claim 10, wherein the at least one inner member extends about a central point of the tip 1.5 or 2.5 times.

14. The tip of claim 10, wherein a radius of the at least one inner member relative to a central point of the tip varies at least a portion of a length of the at least one inner member.

15. A tip configured for use in a skin treatment system, comprising:
    a distal end;
    a proximal end configured to couple to a handpiece assembly;
    at least one hole through which fluid is configured to be conveyed to or away from the distal end;
    an outer member defining a periphery along the distal end; and
    at least one inner member located within an interior area of the outer member, wherein the at least one inner member comprises a spiral-like pattern;
    wherein the at least one inner member is configured to abrade skin.

16. The tip of claim 15, wherein the tip further comprises an imbedded treatment material.

17. The tip of claim 15, wherein the at least one inner member extends about a central point of the tip 1.5 or 2.5 times.

18. The tip of claim 15, wherein a radius of the at least one inner member relative to a central point of the tip varies at least a portion of a length of the at least one inner member.

* * * * *